(12) United States Patent
Fahy et al.

(10) Patent No.: US 6,395,467 B1
(45) Date of Patent: May 28, 2002

(54) CRYOPROTECTANT SOLUTION CONTAINING DIMETHYL SULFOXIDE, AN AMIDE AND ETHYLENE GLYCOL

(76) Inventors: Gregory M. Fahy, 880 Via Blairo; Brian Wowk, 848 Montage Dr., both of Corona, CA (US) 92879

( * ) Notice: Subject to any disclaimer, the term of this patent is extended or adjusted under 35 U.S.C. 154(b) by 0 days.

(21) Appl. No.: 09/400,793

(22) Filed: Sep. 21, 1999

Related U.S. Application Data

(60) Provisional application No. 60/101,194, filed on Sep. 21, 1998, provisional application No. 60/127,158, filed on Mar. 31, 1999, provisional application No. 60/128,142, filed on Apr. 7, 1999, and provisional application No. 60/143,587, filed on Jul. 13, 1999.

(51) Int. Cl.[7] ............................. A01N 1/00; A01N 1/02; C12N 1/04

(52) U.S. Cl. ......................... 435/1.3; 435/1.1; 435/260

(58) Field of Search ........................ 435/1.3, 1.1, 260

(56) References Cited

U.S. PATENT DOCUMENTS

| | | | |
|---|---|---|---|
| 4,559,298 A | | 12/1985 | Fahy .............................. 435/1 |
| 5,047,181 A | * | 9/1991 | Occhionero et al. ........... 264/28 |
| 5,084,377 A | * | 1/1992 | Rowan et al. .................. 435/1 |

FOREIGN PATENT DOCUMENTS

| | | | |
|---|---|---|---|
| JP | 01188311 | * | 7/1989 |
| JP | 01266212 | * | 10/1989 |
| JP | 03130409 | * | 6/1991 |
| JP | 04314769 | * | 11/1992 |
| WO | WO 96/05727 | | 2/1996 |
| WO | WO 96/30459 | | 10/1996 |

OTHER PUBLICATIONS

G. M. Fahy et al., Some Emerging Principles Underlying the Physical Properties, Biological Actions, and Utility of Vitrification Solutions, *Cryobiology*, vol. 24, 1987, pp. 196–213.

Gregory M. Fahy et al., Cryoprotectant Toxicity and Cryoprotectant Toxicity Reduction: In Search of Molecular Mechanisms, *Cryobiology*, vol. 27, 1990, pp. 247–268.

* cited by examiner

*Primary Examiner*—David M. Naff
*Assistant Examiner*—Mike Meller
(74) *Attorney, Agent, or Firm*—Knobbe, Martens, Olson and Bear, LLP

(57) ABSTRACT

A cryoprotectant solution used for preserving biological material comprising cells is disclosed. The solution comprises dimethyl sulfoxide, an amide such as formamide, urea, acetamide, hydroxyurea, N-methyl formamide, and ethylene glycol or ethylene glycol in combination with propylene glycol wherein the propylene glycol replaces less than 8% w/v of the ethylene glycol.

15 Claims, 10 Drawing Sheets

Figure 1
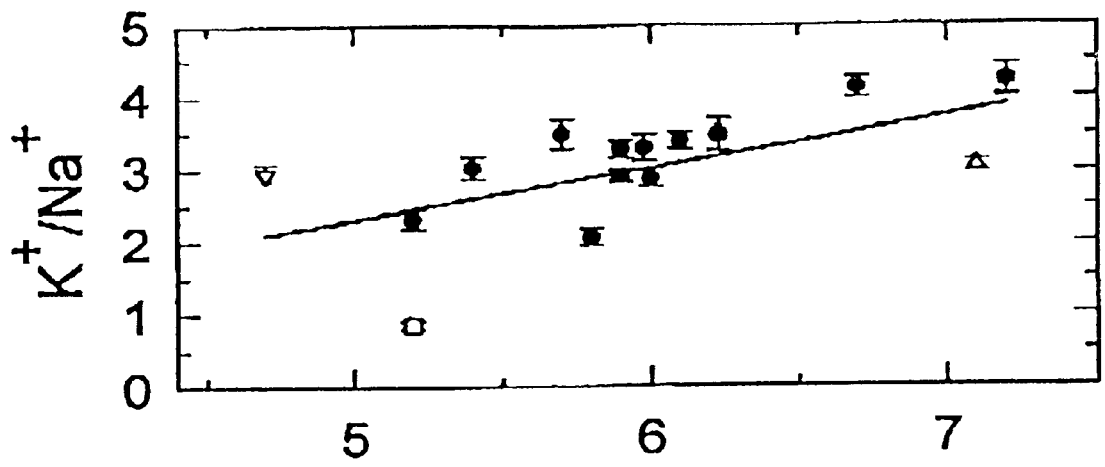
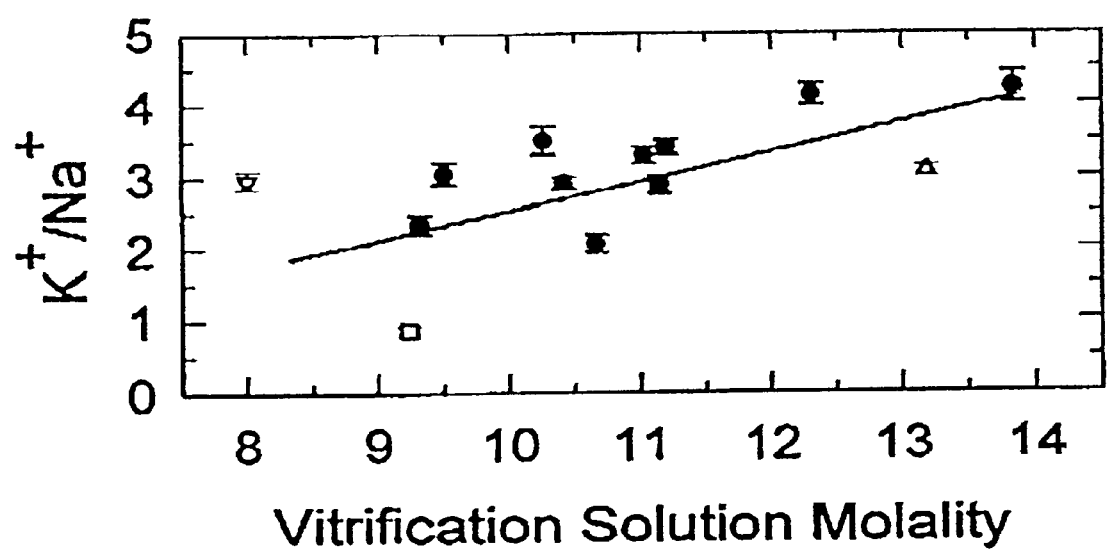

Fig 5
Effect of Varying the EG:D(1)F Ratio
in Vitrifiable Mixtures of D(1)F+EG
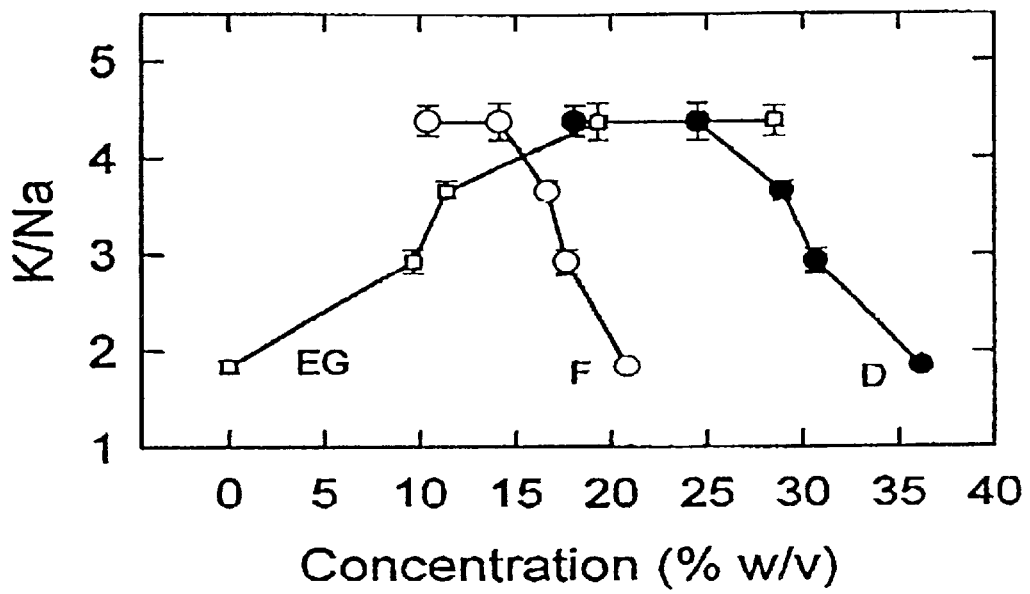
A
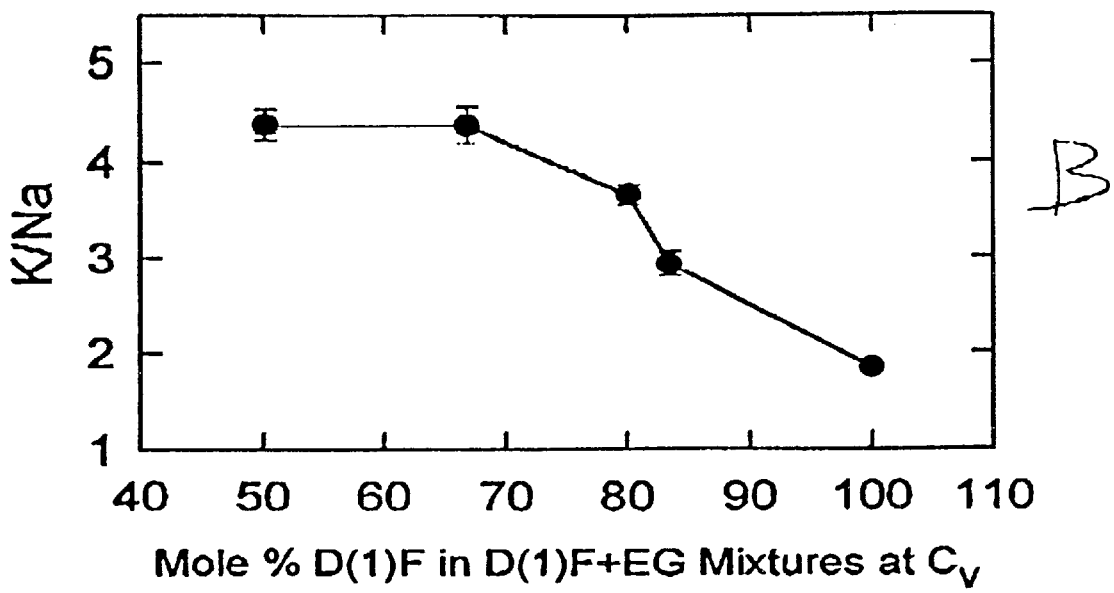
B Variation of Veg Formula
(55% w/v total concentration)

Master Amide Neutralization Graph

CRYOPROTECTANT SOLUTION CONTAINING DIMETHYL SULFOXIDE, AN AMIDE AND ETHYLENE GLYCOL

This application claims the benefit of priority under 35 U.S.C. §119(e) from the following Provisional Application Nos.: 60/101,194, 60/127,158, 60/128,142 and 60/143,587, filed Sep. 21, 1998, Mar. 31, 1999, Apr. 7, 1999 and Jul. 13, 1999, respectively.

FIELD OF THE INVENTION

The invention relates generally to the field of cryobiology. More specifically, the invention relates to method of cryoprotection and novel cryoprotectant solutions and the principles that allow minimization of their toxicity, preferably without substantially weakening their ability to vitrify and to resist devitrification.

BACKGROUND OF THE INVENTION

Cryopreservation refers to the preservation of systems containing living cells at temperatures below the normal freezing point of water (0° C.). The history and literature of cryobiology, the field of science that attempts to understand low temperature biological phenomena and to improve methods of cryopreservation, is large and voluminous, and its successes have touched hundreds of millions of Americans and many others around the world in one way or another over the past 40 years or so. But despite its many impressive successes, cryobiology has still not found ways to cryopreserve transplantable kidneys, hearts, and livers (despite the high value such technology would have) or even many simpler systems, for unlimited times. In many cases, cells such as human and bull sperm and even human corneas can withstand freezing, but with undesirable amounts of injury. For example, up to 95% of human donor semen does not freeze well enough to be used clinically, bull sperm survival is substantially less than 100%, and frozen/thawed corneas perform sufficiently poorly that eye banks generally use simple cold storage in OptiSol™ for short periods in preference to indefinite preservation that could greatly reduce costs and solve many logistic problems. Clearly, there are ample reasons to improve cryopreservation techniques, from both a humanitarian and a commercial viewpoint, yet this has not been accomplished to date.

Fahy proposed, in 1981–1984, that excellent cryopreservation of both simple and highly complex living systems could be attained without ice formation, a process termed vitrification, by using chemical agents known as cryoprotectants in extremely high concentrations (Fahy, Cryobiology 18: 617, 1981; Fahy and Hirsh, in: Organ Preservation, Basic and Applied Aspects, D. E. Pegg, I. A. Jacobsen, and N. A. Halasz, eds, MTP Press, Ltd., 1982, pp. 399404; Fahy et al, Cryobiology 21: 407–426, 1984). As Fahy further explained in 1986, "All of the postulated problems in cryobiology . . . can be solved in principle by the selection of a sufficiently high concentration of cryoprotectant . . . In the extreme case, all ice formation could be suppressed completely by using a concentration of cryoprotectant sufficient to ensure vitrification." Fahy, Cryobiology 23:1–13 (1986).

The potential market for tissue replacements of all kinds, once all problems of supply and rejection have been overcome, has been authoritatively estimated to be in the vicinity of $500 billion per annum. This potential can be realized through a combination of greatly improved control of rejection, enhanced retrieval of natural tissues and organs, and the development of artificial tissues and organs (either engineered tissues and organs or tissues and organs that are simply grown in the laboratory instead of in human bodies), but only if it also becomes possible to cryopreserve the vast number of tissues and organs required to meet this immense market.

Clearly, the value of minimum-toxicity solutions for cryopreservation is vast, and represents a problem that, until now, has not been solved despite the intensive efforts of cryobiologists around the world, who have worked extensively on cryopreservation since the report of the cryoprotective effects of glycerol in 1949 (Polge, Smith, and Parkes, Nature 164: 666, 1949). Fahy himself has described numerous efforts to improve his own vitrification solutions for tissue slices and organs, without progress since the adoption of the VS4-VS41A series around 1986 (Fahy, Levy, and Ali, Cryobiology 24: 196213, 1987; Fahy, Lilley, Linsdell, Douglas, and Meryman, Cryobiology 27: 247268, 1990; Fahy, Cryobiology 35: 344–345, 1997).

SUMMARY OF THE INVENTION

The present application provides cryoprotectant solutions having unprecedented non-toxicity even at higher total concentrations than have previously been contemplated, and while retaining good stability on warming and methods for designing additional examples thereof. By using the principle presented, the user has great flexibility in choosing variations for fine-tuning for the user's particular needs. Further, the invention permits the design of entirely new cryoprotective substances in keeping with the new design principles disclosed herein. The inventors believe this new cryopreservation technology will allow successful preservation of most systems by freezing or by vitrification, especially since it consists not only of specific compositions but also involves several new general principles in cryobiology. The present invention also introduces novel cryoprotectants identified for specific uses based on the general principles and novel uses of previously known cryoprotectants. Both are valuable in identifying best-mode cryopreservation solutions.

The invention provides new theoretical and practical guidelines useful for creating minimum-toxicity vitrification solutions. The invention also provides specific families of vitrification solutions based on these new theoretical insights that have minimum toxicity and that are effective for dissimilar biological systems.

Another aspect of the present invention provides improved solutions for cryopreservation of cells, tissues, organs, artificial organs, artificial tissues, and non-living biological systems. The invention also provides specific families of freezing solutions based on the new vitrification solutions.

The invention provides cryoprotectant solutions and methods that also have applications in preservation by freezing point depression, supercooling, and cold storage. The invention also provides specific solutes and combinations of solutes that, when used in the proper way, have wholly unforeseen beneficial effects (reduced cryoprotectant toxicity, enhanced vitrification tendency, and enhanced resistance to devitrification).

New ways of, and new agents for, inhibiting the growth of ice crystals in aqueous solutions and in other contexts are described herein. The invention provides methods for scaling up the vitrification of small biological systems for use on large biological systems with minimal or no required increases in the concentrations of standard cryoprotectants.

The invention further provides cryoprotectant solutions that, very surprisingly, have no gap between the concentration that vitrifies and the concentration that can be warmed at modest rates without devitrification.

BRIEF DESCRIPTION OF THE DRAWINGS

FIG. 1 shows the toxicities (measured by reductions in tissue K+/Na+ratio) of 13 vitrification solutions for rabbit renal cortical slices.

FIG. 5 shows the data of FIG. 4 plotted in terms of the absolute concentrations of DMSO, formamide, and ethylene glycol in the solutions, as well as in relation to the mole percentage of D(1)F in the mixture.

DETAILED DESCRIPTION OF THE PREFERRED EMBODIMENTS

Figure 2:
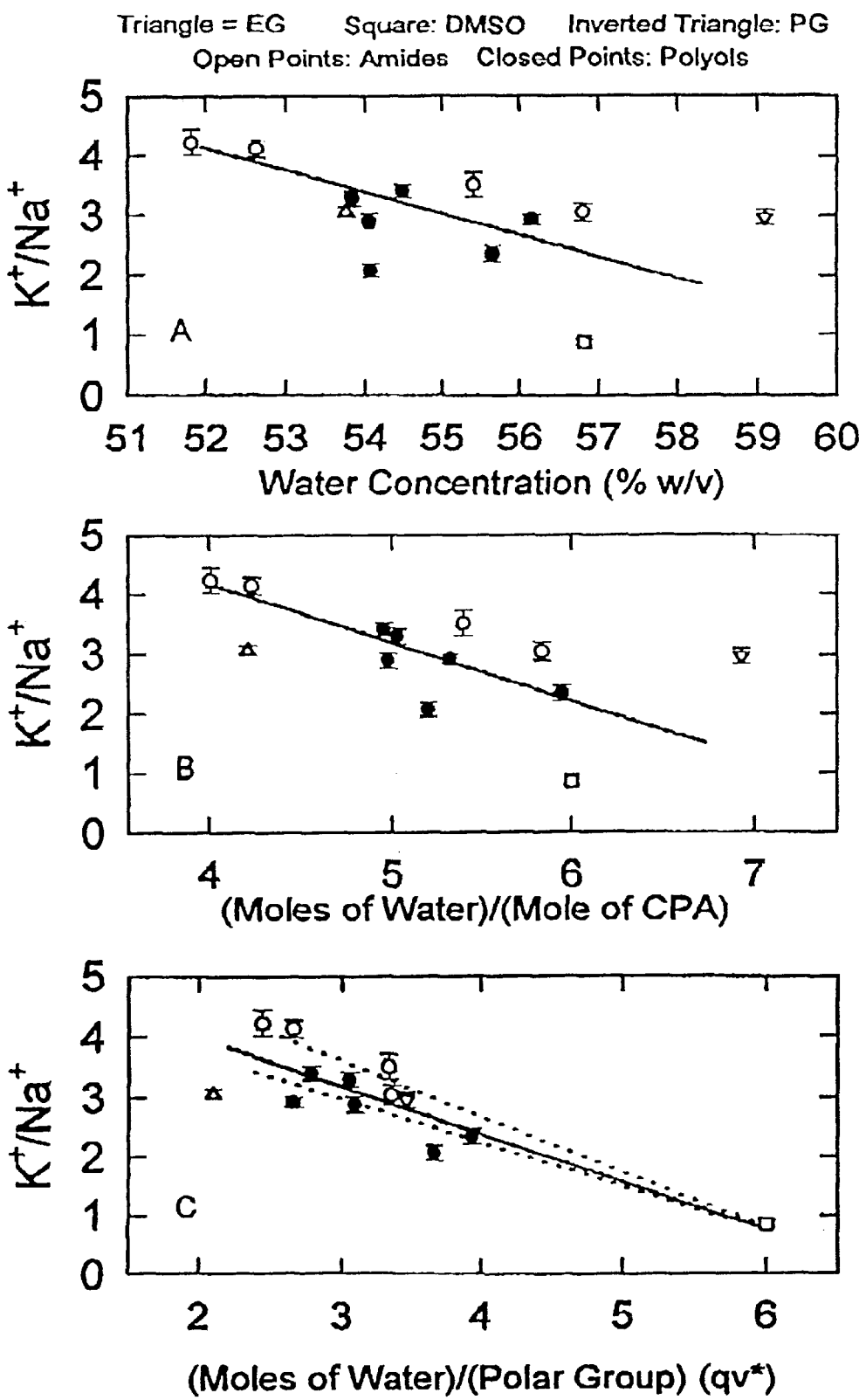
FIG. 2 represents the toxicity data of FIG. 1 in relation to the water content of the solution.

One aspect of the present invention relates to a broad family of rationally-composed and balanced cryoprotectant mixtures that provide minimum-toxicity compositions for the cryopreservation of proteins, organelles, cell extracts, cells, tissues, blood vessels, organs, and artificial or engineered cells, tissues, blood vessels, organs or organoids, organisms, or other biological systems by vitrification, freezing, and other means, and the associated principles that govern the rational formulation of superior cryoprotectant solutions. It is believed that the present invention will allow the practitioner of ordinary skill in the art to select a cryopreservation solution for use that will surpass the value of his or her prior cryopreservation solution. It is also believed that a licensor of the present disclosure, given a request for assistance with a cryopreservation problem, will be able to modify the examples provided according to the principles contained herein and a straightforward consideration of the biology of the system to be preserved to produce a specific version that will be particularly applicable to the system of interest.

To date, vitrification applied according to Fahy's basic approach described in the Background of the Invention has been successfully used for a wide variety of living systems (for example, Rall and Fahy, Nature 313: 573575 1985; Takahashi et al., Cryobiology 23, 103–115, 1986; Fahy, in: Low Temperature Biotechnology: Emerging Applications and Engineering Contributions, J. J. McGrath and K. R. Diller, eds, ASME, 1988, pp. 113146). However, in general vitrification has not been widely employed outside the field of embryo cryopreservation because of the toxicity of the high cryoprotectant concentrations needed for the process, which often makes the method awkward, difficult, or impossible to apply. Particularly disappointing is that Fahy's vitrification approach was motivated primarily by the desire to bank complex systems such as mammalian organs at temperatures below −100° C. Yet in 1998, 17 years after the initial proposal, this goal has still not been attained. We believe that the reason is that currently available cryoprotectant solutions remain too toxic to permit 100% survival of organs treated with such solutions, even without cooling to and warming from cryogenic temperatures.

The problem of reducing cryoprotectant toxicity does not pertain only to cryopreservation by vitrification. As Fahy also pointed out (Fahy, Cryobiology 17:371388, 1980; Fahy, CryoLetters 4: 309314, 1983; Fahy, Cryobiology, 21: 407–426, 1984; Fahy, Cryobiology 23: 1–13, 1986), freezing produces high concentrations of cryoprotectants due to the removal of pure water from the solution in the form of ice, apparently leading to toxicity similar to that experienced when cells are exposed to solutions capable of vitrification. For this reason, less toxic solutions for freezing cells and tissues would also be beneficial, particularly given that the quantity of cells frozen on a routine basis for all applications is astronomical.

Vitrification solutions developed by others (primarily for embryos or plant cells) sometimes give recoveries of 80% or more, but this is deceptive. All of these solutions require rapid addition and removal of the cryoprotectant, and typically involve exposure to the vitrifiable solution for around two minutes or less. The effect of this minimal-exposure regimen is to mask the otherwise severe intrinsic toxicity of these solutions, but such brief exposure constraints limit the use of such vitrification solutions to small samples. In contrast, when attempting to vitrify organs, one requires cryoprotectant solutions that can be in contact with cells for relatively long times (circa, 40 minutes) at their peak concentrations, and so the solutions must be intrinsically less toxic. Sometimes recoveries approaching ~90% or more have been obtained for isolated cell systems, but this often or even only occurs in circumstances in which there appears to be either a unique resistance of the system being studied to a particular cryoprotectant, which means that the same solution, applied to other systems, would not be effective, or, again, when only brief exposures are permitted.

Furthermore, most systems that survive vitrification can be warmed at very rapid rates by conduction methods. This is generally essential because solutions that vitrify generally require warming rates on the order of about 1,000° C./min to escape from devitrification (crystallization upon warming) (Fahy, in The Biophysics of Organ Cryopreservation, A. M. Karow, Jr., and D. E. Pegg, Eds., Plenum Press, 1987), rate sufficiently high as to be unattainable for many systems and in many settings. This problem has prevented the application of otherwise successful vitrification methods to, for example, human corneas (Bourne, 1994).

Because many cells do not survive well with available cryopreservation techniques despite the opportunities that exist for circumventing toxicity as just noted, excellent cryopreservation solutions derived from work on organ cryopreservation, for which excellent solutions are mandatory, are likely to find applications for many other systems. For many years, a solution called VS41A has been used in experiments on rabbit kidney cryopreservation. It is believed by its inventor (G.M.F.) to be less toxic than most or all other available and relevant vitrification solutions, and it has allowed about 50% survival of rabbit kidneys after perfusion with VS41A and transplantation with immediate contralateral nephrectomy (Fahy, in: Advances in Anti-Aging Medicine, Vol. 1, R. M. Klatz, ed., Mary Ann Liebert, Inc., Larchmont, N.Y., pp. 249–255, 1996), but 50% survival is not sufficient.

There is no current ability to predict with confidence which cryoprotectant solutions will be effective and which will be ineffective for any unfamiliar living system, and there is no method other than random experimentation and guessing for deriving more promising formulae to test. This has greatly limited work on developing cryoprotectant solutions. It has also given the entire field a lack of direction and has resulted in a prevailing state of confusion that has prevented rapid advances.

The number of potential combinations of cryoprotectants in various proportions is nearly infinite, so the discovery of particularly advantageous formulae is not likely without undue experimentation. It is clear that there can be no obvious ways in the prior art of solving the problem of designing generally-applicable, acceptably-stable, minimal-toxicity cryoprotectant solutions given these problems, the level of effort already expended unsuccessfully, and the unclaimed enormous potential rewards for success.

As indicated already, one reason better solutions have not been developed until now is the lack of any systematic knowledge concerning the mechanisms and modulators of the toxicity of cryoprotectant solutions (Fahy, Lilley, Linsdell, Douglas, and Meryman, Cryobiology 27: 247268, 1990). New information is needed to permit more enlightened choices to be made for reducing the toxicity of cryoprotectant mixtures.

The first step to choosing minimum-toxicity solutions for cryopreservation, surprisingly, is to choose agents that vitrify aqueous solutions "poorly," meaning that relatively high concentrations of cryoprotectant water bonding sites are required relative to water to prevent ice formation. This means that these solutions contain relatively little water compared to more strongly glass-forming solutions. This should make such solutions more toxic according to the traditional wisdom in the field of cryobiology, and is counterintuitive given that cells require water for stabilizing delicate cell proteins and membranes. Nevertheless, we show herein for the first time that the opposite is true, i.e., that these are the best solutions, not the worst solutions as commonly believed, for avoiding toxicity.

While not wishing to be bound by any theory, we postulate that this phenomenon is explained by weak cryoprotectant-water interactions. Weak cryoprotectant-water interactions imply that more cryoprotectant will be needed to immobilize water sufficiently to form an aqueous glass, but also imply that the water that remains can more readily break its bonds with the cryoprotectant and therefore better hydrate life-critical molecules composing living cells. In other words, although water content is lower than in standard vitrification solutions, water availability for hydrating living cells is, paradoxically, greater than in standard vitrification solutions, the biological molecules competing successfully with the cryoprotectant for access to water. This critical conclusion is not inferable and has not been previously inferred from the prior art.

Having kept the water content of the solution to a minimum by using poor glass formers, optimum cryoprotectant solutions may optionally include polymeric materials of about 1,000 daltons to 50,000 daltons in relative molecular mass in place of variable amounts of penetrating cryoprotectant so as to permit a reduction in intracellular cryoprotectant concentration and, thereby, an effective further increase in intracellular water availability. These polymers may or may not include polymers capable of specifically blocking ice nucleation or ice growth. Further, the solutions may also contain low molecular mass agents (less than 1,000 daltons in relative molecular mass) that are able to specifically inhibit the nucleation and/or growth of ice.

As first proposed and demonstrated by Fahy et al. (Cryobiology, 21: 407–426, 1984), cells contain vitrification-enhancing proteins and therefore cytoplasm does not require the full amount of penetrating cryoprotectant that may be needed to vitrify the extracellular space. Generally speaking, however, it is not obvious that this principle can be used to allow a solution that is unable to vitrify to be vitrified by reducing the concentration of penetrating agent still farther. Examples are provided herein wherein this approach is demonstrated for the first time. This strategy is effective in reducing injury to the cell as a whole, provided it is not carried so far as to exacerbate devitrification.

The use of npCPAs to enhance vitrification is routine, however, our addition of the use of npCPAs in combination with weakly glass-forming cryoprotectant combinations is not. We also added the use of relatively low molecular mass npCPAs as taught here for the first time. Lastly, the combination of relatively low molecular mass npCPAs and weakly glass-forming cryoprotectant mixtures is new. Finally, the combination of all modalities (weak glass-formers, npCPAs or low mass npCPAs (ImnpCPAs), and ice blocking agents) is still more remote from the prior art.

The concept that concentrations affect living cells has always been complicated by the fact that there has never been any theoretical basis for determining which concentration scale is meaningful for toxicity. This is particularly problematic in cryobiology, in which the cryobiologist uses terms such as "solution effect" injury, but without being able to determine which aspect of the solution composition is governing the injury. Biologists and chemists may think that a given concentration scale has meaning, but the cell response may not be proportional to that scale. By providing a clearly superior concentration scale for relating solution composition to cell viability in a manner that has never before been possible, the practitioner of the art will be able to contemplate cryoinjury and cryoprotection in a manner never before possible.

In summary, some features of the invention are as follows. These features will be explained in more detail later.

A) The $q^*$ method of discovering new, favorable cryoprotectant formulae (the $q^*$ scale is moles of water per mole of polar group on penetrating cryoprotectants in the solution; the reciprocal of $q^*$, $q^*-1$, can also be employed). The name $q^*$ was chosen for the parameter "moles of water per mole of polar group" to distinguish between it and Q, which is moles of cryoprotectant per 10 moles of water (e.g., Fahy et al, Cryobiology 21: 407–426, 1984), and $q^*$ at Cv is $qv^*$.

The $qv^*$ method for identifying useful cryoprotectant solutions based on this concentration scale is: to select at least one cryoprotectant whose $qv^*$ is below 2.0, include it in a mixture with other cryoprotectants, determine the Cv of the resulting mixture in the normal way (see, for example, Fahy et al, Cryobiology 21: 407–426, 1984), calculate $q^*$ at Cv ($qv^*$) (note: the number of moles of water can be readily determined from the weight of a given volume of solution minus the number of grams of all solutes, i.e., from the number of grams of water per unit volume or per unit weight), compare the resulting qv* value to the qv* values of alternative cryoprotectant solutions, and selecting lower qv* value solutions in general preference to higher qv* solutions. qv* values can be estimated adequately from published Q values by estimating that the densities of all solution components as pure substances are unchanged by being in solution with other substances (the validity of a similar approach in deriving Q from % w/v concentrations is discussed in Fahy, in: Low Temperature Biotechnology: Emerging Applications and Engineering Contributions, J.J. McGrath and K. R. Diller, eds, ASME, 1988, pp. 113146.)

A variant on this method is to determine q* at the concentration giving acceptable and consistent rates of devitrification, and base comparisons on this q* (qd*).

For understanding freezing injury, it will be possible to calculate q* for different solutions at the same water activity (qa*, which can be determined when cells are frozen to the same temperature), and rank the resulting freezing injury on the basis of the qa* values. This will allow superior freezing solutions to be developed. Furthermore, qa* can also be used to select candidate solutions for preservation by freezing point depression at a given temperature, since, again, solutions having the same freezing point have the same water activity, providing a meaningful basis for comparison of q* values between different solutions.

Another variant on the method is to select solutions for supercooling based on the q* values for solutions that are just concentrated enough to permit the desired degree of supercooling (qs*).

In summary, the q* method will allow superior preservation by vitrification, freezing, freezing point depression, and supercooling. Further, solutions found for these applications may also be applied in low concentrations (below about 4 molar) to stabilize cells, tissues, and organs at temperatures above their equilibrium freezing/melting points (Tm) to prolong liquid state storage at these temperatures (cold storage).

B) Solutions that include primarily a combination of dimethyl sulfoxide and at least two weak glass-forming agent(s), one of which may be an amide and one of which may be ethylene glycol, with or without a variety of other low and higher molecular weight cryoprotectants to facilitate vitrification and inhibit devitrification.

C) Optional use, within the polymer component of the solution, of one or more forms of polyvinyl alcohol (PVA) as practical ice blocking agents in the presence of other cryoprotectants.

D) Optional inclusion, within the polymer component of the solution, of one or more polymers ranging in molecular mass from about 800 to about 5,000 daltons to enhance vitrification and inhibit devitrification.

E) Optional inclusion of low molecular weight ice inhibiting agents.

All of these different but interacting elements of cryopreservation solution formulation combine to provide a truly powerful capability for avoiding injury during and after cryo- or cold preservation, with expected broad practical and commercial utility.

Definitions

Specific terms to be used herein are used as defined below. Terms not specifically defined are intended to have the normal meanings attributed to such terms according to general usage in the field of cryobiology.

"q*" is the number of moles of water in a cryoprotectant solution per mole of polar groups present on penetrating cryoprotectants in the solution.

"qv*" is q* for solutions at their Cv.

"qa*" is q* for solutions at a standard water activity (generally established by freezing to a standard temperature).

"qd*" is q* for solutions that exhibit a standard devitrification tendency.

"qs*" is q* for solutions that exhibit a standard supercooling tendency in the presence of a standard amount of a nucleation inhibitor or ice crystal growth inhibitor, such as PVA for nucleation inhibition and antifreeze protein for crystal growth inhibition or thermal hysteresis induction.

"Cv" is the concentration needed to vitrify 5–10 ml of solution at a cooling rate of about 10° C./min.

"Vitrification" is defined to mean the solidification of a liquid solution as a glass rather than by freezing.

"Glass" is defined herein to mean a liquid solution whose molecular motions have been virtually arrested by cooling to below the glass transition temperature of the solution.

"Devitrification" means the formation of ice during the warming of a previously deeply cooled or vitrified solution (this is not the reverse of vitrification; the reverse of vitrification has been called "vitromelting" or simply "liquefaction").

"Cryoprotectants" are chemicals that reduce damage associated with cryopreservation.

We recognize penetrating cryoprotectant(s) (pCPAs) as cryoprotectants that cross the cell membrane on a reasonable time scale (seconds to tens of minutes). Nonpenetrating cryoprotectant(s) (npCPAs) remain extracellular under most practical conditions.

"Cryopreservation" is preservation of biological systems by freezing, vitrification, supercooling, or freezing point depression.

"Supercooling" is cooling to a temperature below the equilibrium melting point, but above the glass transition temperature, without actually freezing the sample.

Preservation by "freezing point depression" is the use of a cryoprotectant to reduce the melting point of an aqueous solution to below 0° C., and to store a biological system (for example, a protein or an organ) within about plus or minus 3 degrees of that melting point, but below 0° C.

"Cold storage" refers to storage above the melting point of the solution, typically at 0° C. or above but in the presence of a cryoprotectant or cryoprotectant mixture used to stabilize the biological system.

"Ice blocking agents" are chemicals that reduce or eliminate ice formation particularly well during cooling, warming, or isothermal holding, either by bonding directly to ice at the ice-liquid interface or by preventing nucleation, or by other means.

"Thermal hysteresis" is or refers to the difference between the melting point of the solution and the temperature at which ice can grow at appreciable rates during cooling below this temperature. It has been shown that when a-axis-bonding ice blockers are present, ice growth is prevented or greatly inhibited despite the presence of ice below the melting point, until the low temperature limit for this effect is reached, which defines the magnitude of the thermal hysteresis in that case.

"Antifreeze proteins" (or AFPs, also called "thermal hysteresis proteins" or THPs) are natural proteins made in living systems that create thermal hysteresis effects.

"VS41A" is a cryoprotectant solution known in the art and containing dimethyl sulfoxide, formamide, and 1,2-propanediol (propylene glycol, or PG) such that the total concentration of these three cryoprotectants is 55% w/v, the molar concentration of dimethyl sulfoxide equals the molar concentration of formamide, and the concentration of PG is 16.84% w/v. VS41A is considered to be the least toxic vitrification solution known for mammalian organs.

"VS4" is a diluted version of VS41A containing 6% w/v less penetrating cryoprotectant than VS41A and that can be vitrified using an applied pressure of 1,000 atmospheres.

A "carrier" or "vehicle" solution is the portion of a cryoprotectant solution other than the cryoprotectants that are present in the solution; the "carrier" or "vehicle" solution is generally also used in the absence of cryoprotectants to support the viability of cells, organs, or tissues outside of the body.

The invention will be described in greater detail below.

Cryoprotectant Solutions

We have found that the best cryoprotectant solutions contain three interacting parts: 1) penetrating cryoprotectant(s) (pCPAs), 2) nonpenetrating cryoprotectant(s) (npCPAs), and 3) high or low-molecular weight specific ice-blocking cryoprotectant(s) (ibCPAs).

Within the scope of the present application, the ice-blocking substances cannot generally be used successfully without other cryoprotectants for cryopreservation or to form cryopreservation solutions, except that they can be used for cryoprotectant-free supercooling to temperatures above about $-20°$ C. A detailed description of the novel ice-blocking properties of PVA is contained in a companion U.S. patent application, entitled "polyvinyl alcohol compounds for inhibition of ice growth", filed Sep. 21, 1999, which is incorporated herein in its entirety by reference. Reference to "polyvinyl alcohol" or "PVA" herein is intended to represent all forms of polyvinyl alcohol identified as being potentially useful in this companion application. However, to summarize, polyvinyl alcohol and related compounds were found to inhibit the freezing of water and water solutions. These synthetic compounds preferentially bind and inhibit ice nucleating surfaces in a manner similar to natural antifreeze proteins. The resulting inhibition allows water and water solutions to supercool without ice formation to temperatures below the thermodynamic freezing point. The freezing inhibition occurs at concentrations as small as one part per million, although concentrations up to one part per hundred are preferred. These polyvinyl alcohol additives are very useful for enhancing the performance of antifreeze formulations, biological cryopreservation solutions, and for preventing frost damage to plants and other industrial products and processes. The related compounds include any compounds with the formula $[-CR_2CROH-]_n$ where R is any atom, or group of atoms, except a hydroxyl group, and $n \geq 3$. In addition one or more of the hydroxyl groups can be replaced with chemical groups such as methoxyl, alkoxyl, and amine groups. The polyvinyl alcohol compounds preferably have a MW less than 1000 kDa, more preferably less then 10 kDa and even more preferably 130–2000 daltons. The polyvinyl alcohol compounds preferably contain 1 to 25 mole percent vinyl acetate, more preferably 10–20 mole percent vinyl acetate and they can be atactic or syndiotactic.

The pCPA and npCPA mixtures are highly useful without ice-blocking substances, but require the use of ice-blocking substances in many best-mode solutions. In summary, ideal solutions for cryoprotection involve the use of all three elements of the invention in combination with one another, and less best mode but still excellent solutions can be obtained by using just one or two of these principles. For example, corneas are believed to be impermeable to polymers such as PVA, and require pCPAs with or without additional non-ice-blocking npCPAs or the use of ice-blocking npCPAs primarily as osmotic agents.

The Theory Involved

Water is necessary for life, but the data in the examples below show higher survival with reduced water per mole of polar group in the solutions. How is this possible? Stated another way, we know that the toxicity of a given pCPA rises as its concentration rises, so how can higher concentrations in general result in lower toxicity?

While not wishing to be bound by any theory, a plausible explanation is that the number of water molecules associated with polar groups in some vitrification solutions is much less than the number of water molecules associated with polar groups in other vitrification solutions. In other words, in the former solutions the polar groups are less strongly hydrated. Because all water in all solutions vitrifies on cooling, all water is perturbed in all solutions, but a strongly-perturbing polar group must therefore perturb more water per mole than does a weakly-perturbing group, and this stronger perturbation is associated with greater toxicity. The surprising implication is that although less water is present in the weakly-perturbed solution, the water that remains is more available, on average, to sustain biological viability than the water that remains in the more water-rich but also more water-perturbed solutions.

This is a wholly unprecedented and unpredicted observation with a practical implication: for best results, cryoprotectants or cryoprotectant mixtures should be chosen that are poor vitrifiers. This is the exact opposite of the standard approach to developing good solutions for vitrification of living systems. It is still true that, for a given cryoprotectant or mixture, one should not use a higher concentration than is needed for vitrification, since this will reduce, not increase water availability. But given a choice between two solutions that vitrify at different concentrations, the solution that vitrifies at a higher concentration will tend to have less toxicity than the other solution, provided other factors do not come into play.

One factor that does tend to come into play is specific toxicity. For example, formamide is highly toxic compared to most cryoprotectants, but its toxicity can be fully neutralized by the addition of dimethyl sulfoxide (Fahy, da Mouta, Tsonev, Khirabadi, Mehl, and Meryman, in: Cell Biology of Trauma, J. J. Lemasters and C. Oliver, eds., CRC Press, 1995, pp. 333–356). Addition of ethylene glycol to formamide has no protective effect, so that even though a mixture of formamide and ethylene glycol vitrifies at a high concentration (Fahy, in: Low Temperature Biotechnology: Emerging Applications and Engineering Contributions, J. J. McGrath and K. R. Diller, eds, ASME, 1988, pp. 113146), the solution is extremely toxic. Similar comments apply to particularly hydrophobic or detergent-like compounds, as is well known to skilled practitioners in the art. Finally, the more hydrophobic a molecule is, the more weakly it will tend to interact with water but, as is known in the art, excessive hydrophobicity leads to toxicity and must be avoided. Furthermore, some living systems are particularly sensitive to specific cryoprotectants, one example being the sensitivity of the kidney to glycerol, which is a poor glass former but is both rather poorly penetrating and capable of directly entering into biochemical pathways to produce biochemical disturbances (for example, see Burch et al., J Biol Chem 245: 2092–2102, 1970, and Jans and Willem, Eur J Biochem 174: 67–73, 1988).

Another factor that could come into play is reduction of the water content below a minimum value required for adequate hydration of biomolecules even in the presence of weak water-cryoprotectant interactions: presumably, there is an upper limit beyond which weak glass-forming ability becomes detrimental rather than beneficial. However, the Examples show that even very low qv* solutions (qv*<1.6) have low toxicity.

Practitioners of ordinary skill in the art are aware of such pitfalls and are able to avoid them. In any case, if solutions are mistakenly chosen for testing on the basis of having a low qv* and are found to be toxic, they can be put aside in favor of low qv* solutions that are indeed less toxic than prior art solutions. The important result is that superior solutions will generally be found using the q* method that would not otherwise be found, and this discovery of good solutions for permanent use is a more important benefit than the detriment of transiently testing occasional trial toxic solutions.

We believe the invention is sufficiently described by the above brief description and a series of examples that illustrate specific valuable solutions, specific metes and bounds, and specific guiding principles that are considered part of the invention. For this reason, the bulk of the detailed description of the invention is taught in the form of several specific examples.

EXAMPLE 1

Prediction of Toxicity using qv*: Solutions that Vitrify at 1000 Atmospheres in the Presence of 6% w/v Polymer FIGS. 1 and 2 display a reanalysis (performed in early July of 1998) of public information (Fahy, Levy, and Ali, Cryobiology 24: 196213, 1987) on the toxicity of several vitrification solutions of known composition. These vitrification solutions will vitrify at 1,000 atmospheres and contain either 6% polyvinyl pyrrolidone of relative molecular mass 40 kDa [PVP K30] or 6% polyethylene glycol [PEG 8000]. The data set is advantageous because all solutions analyzed are vitrifiable, the data set has low standard errors, and toxicity was convincingly dissociated from osmotic factors (see Fahy, Levy, and Ali, 1987, for discussion). In this example, viability was defined by the ratio of primarily intracellular potassium to intracellular sodium (K/Na ratio) after cryoprotectant washout and active metabolism for 90 min at the optimum temperature of 25° C. The test system was rabbit renal cortical slices.

Despite some correlation between the toxicity of the solutions and both higher and lower concentrations of dimethyl sulfoxide (DMSO) in the solutions, the published paper containing the data revealed no single, satisfying general theory that could account for the observed toxicity data as a whole. Nor was there any reason to believe that there should or could be such a theory (see Fahy, Lilley, Linsdell, Douglas, and Meryman, Cryobiology 27: 247–268, 1990, for discussion).

In FIG. 1 the toxicities are related to the total concentrations of the penetrating cryoprotective agents (pCPAs) needed for the solutions to vitrify (Cv). Cv was measured at 1,000 atmospheres of pressure and in the presence of 6% w/v PEG or PVP and is expressed in molar or molal units. Some indication of a novel trend was discerned (FIG. 1): oddly, if anything, the solutions that required higher concentrations to vitrify also appeared to have lower toxicities at their Cvs. However, such a trend would be destroyed by changing just a few points out of the many plotted, and contradicts the prevailing assumption that the more concentrated a solution is, the more toxic it is. There is also no hint from these plots that hydration of biomolecules has anything to do with the toxicity of the solutions. If anything, it would normally be presumed that the net interaction between water and cryoprotectant must be the same in all of these solutions, since the solutions are all presumably equally vitrifiable. The plot does reveal, however, that the typical assumption that the best solutions for vitrification are those that vitrify at the lowest concentrations, is baseless, in that recovery instead appears to be similar regardless of the Cv.

FIG. 2 represents the toxicity data of FIG. 1 in relation to the water content of the solution, the number of moles of water in the solution per mole of pCPA in the solution, and the number of moles of water per mole of hydrogen-bonding groups that are present on the penetrating cryoprotectants in the solution (qv*). As shown in FIG. 2, the correlation is little better when viability is plotted against either the water content of the solution (A) or the number of moles of water per mole of cryoprotectant (B). However, when the number of polar groups per mole of pCPA in each solution is summed and viability is plotted against the average number of moles of water per mole of polar groups (OH, C=O, NH2, S=O) on the pCPAs in the solution (q*), there is an astonishing convergence of results (FIG. 2C). For the first time, this plot yielded a good correlation between a solution compositional variable and the toxicity of multiple vitrification solutions. Amazingly, even DMSO as a monoagent (open square) fitted into the overall pattern as an anchor point for the data, rather than being the major outlier it has always been in the past.

The general fit between the data and qv* implies that amides may be frequently advantageous mostly because they lower the qv* of the solution more than most other solutes, a wholly novel explanation for their utility. However, the dashed lines in FIG. 2C segregate the viability-qv* relationship into amide-dominated (open circles) and polyol-dominated (filled circles) solutions, and show that the two data sets may be separate, the viability always being somewhat higher for a given qv* in the presence of amides than in their absence. Although this trend bears further examination, the primary result is that all solutions, whether they contain amides or not, obey the general qv* rule.

There is at least one discrepancy. In this data set, solutions based entirely on ethylene glycol (EG, open triangle) were identical in toxicity to solutions based entirely on propylene glycol (PG, inverted open triangle), despite extreme differences in their qv* values both at 1 atm and at 1000 atm. This could indicate that these solutes do not obey the qv* rule, or it could indicate that these particular data points are erroneous, or that the qv* value for EG as a monoagent is too low. However, the examples below indicate that both EG and PG are in compliance with the viability-qv* phenomenology, and that the outlying points in FIG. 2, lower panel are not representative but are instead misleading. This makes the discovery of the qv* phenomenon doubly non-obvious, as the phenomenon was discovered from a data set with at least one very misleading point.

EXAMPLE 2

Viability Correlates with qv* in Disperate Solutions

Figure 3:
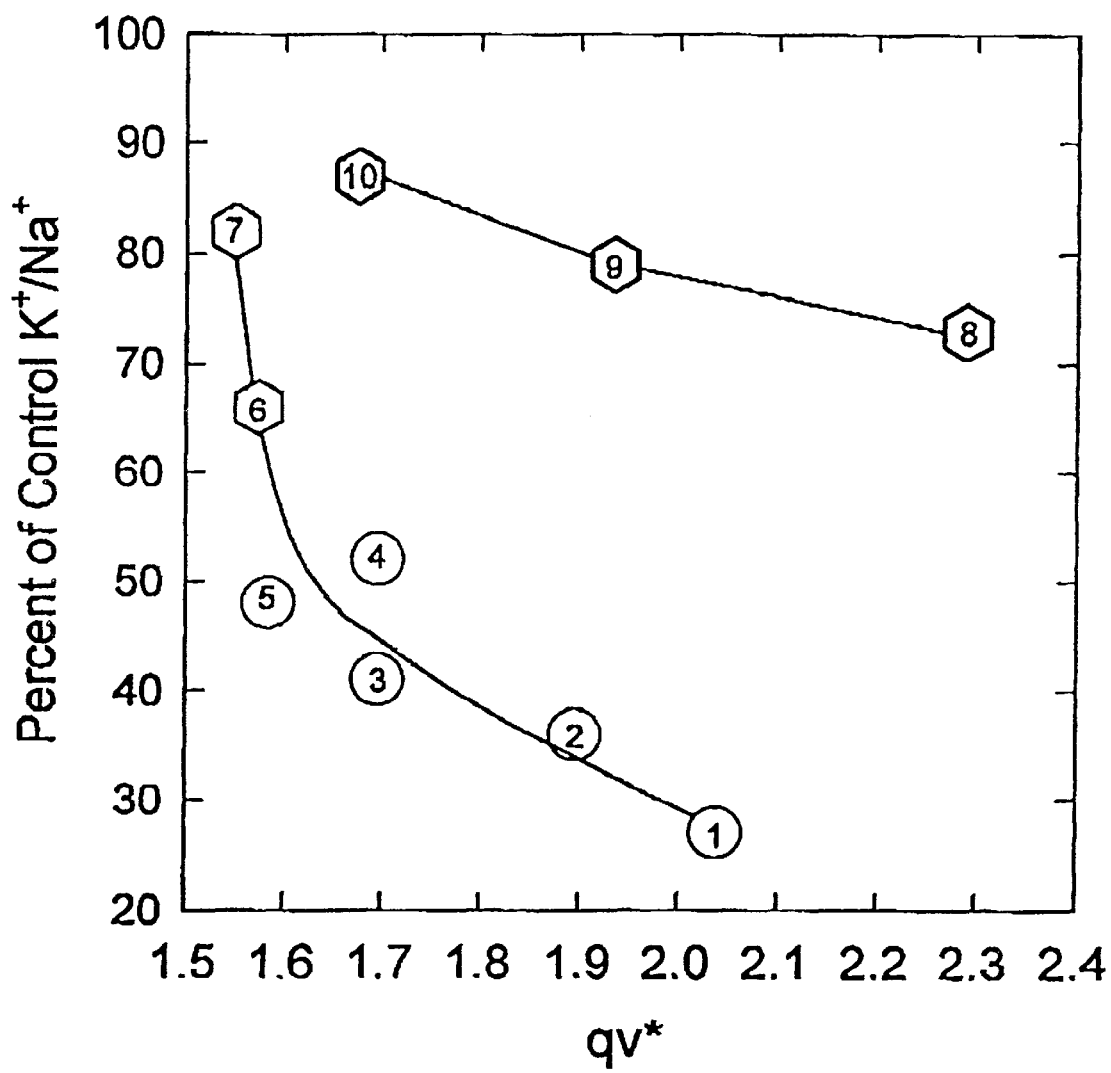
FIG. 3 shows a retrospective analysis of viability data in terms of qv*.

FIG. 3 shows two curves displaying the results of two separate experiments. It shows a retrospective analysis of viability data in terms of qv*, showing a) a good correlation between viability and qv* for solutions very different from those in FIG. 2, and b) an elevation of viability when qv* is increased using polyvinyl alcohol to inhibit nucleation.

Points 1–5 were done in a EuroCollins vehicle solution and consisted of a systematic variation in the proportion of EG:3-methoxy-1,2-propanediol or 2-methoxyethanol in comparison to VS41A, whereas points 6–10 represent experiments carried out in the presence of a vehicle solution called GHP-2 with (points 8–10) or without (points 6 and 7) 1% PVA of about a 7,000 dalton average molecular mass. Several points are illustrated in this example. First, VS41A, point 1, yielded poor results in this experiment. Pure ethylene glycol (which had a Cv of 54% w/v in EuroCollins solution, point 5) yielded less than 50% recovery, but as it was replaced with more and more 3-methoxy-1,2-propanediol (MG; points 4 and 2 are 3 parts EG to one part MG and 1 part EG to 3 parts MG, respectively, at 53 and 52% w/v Cv values, respectively) or with 2-methoxyethanol (2-ME; point 3 represents 3 parts EG to 1 part 2-ME, Cv=53% w/v), the results became worse. Yet the data could be well fitted by reference to the qv* of these solutions, despite the lack of inclusion of either MG or 2-ME in the analysis of FIG. 2C. Furthermore, data collected 8 experiments later, involving very different solutions (point 6 represents 58.5% w/v D(1)UE20+6% w/v PVP 5000, where "E20" means there are 20 grams per deciliter of EG and the (1) indicates that the balance of the 58.5% w/v pCPA is composed of a 1:1 mole ratio of DMSO to urea; and point 7 represents 55% E[D(0.7)F]38.18+6% PVP 5000, meaning that 38.18% w/v of the solution consists of a mixture of DMSO and formamide in a ratio of 0.7 moles of DMSO per mole of formamide, and EG is present at a concentration of 55−38.18=16.82% w/v) falls on the same curve as points 1–5. Points 8–10 illustrate the fact that biological systems survive better when they are more fully hydrated despite being vitrifiable, thanks to the antinucleation abilities of PVA, which permit the amount of penetrating CPA to be reduced without preventing vitrification. Point 8 consists of VS4 (see below) rendered vitrifiable by the inclusion of 5% PVP at Mr 5000 plus 1% PVA at Mr 7000 daltons. Although the viability is excellent, it is worse than the viability of a solution (point 9) composed of Veg–4% D(1)F+5% PVP 5000 plus 1% PVA 7000 (see definition of Veg below). Finally, point 10, which represents the effects of 53% E[D(0.7)F]38.18+5% PVP 5000+1% PVA 7000 (same notation as above), yields better results still. Both solutions 9 and 10 lack the strong glass-former 1,2-propanediol, which is present in VS4, and consequently points 9–10 are consistent with analysis on the basis of qv*.

EXAMPLE 3

The Toxicities of Pure CPAs Relate to qv*

Table 1 recapitulates the six nominally weakest glass-forming solutes described in the most recently-published compendium of glass-forming compounds provided by Fahy (Fahy, in: Low Temperature Biotechnology: Emerging Applications and Engineering Contributions, J. J. McGrath and K. R. Diller, eds, ASME, 1988, pp. 113146). Toxicity data is limited for these solutes, but at least two such solutes have been evaluated adequately. Acetamide, which is the weakest glass former in Table 1 based

TABLE 1

Some Weakly Glass-Forming Cryoprotectants

| Weak Glass-Forming CPA | Q (moles of CPA per 10 moles of water) | Moles of water/mole of CPA (10/Q) | Moles of Polar Groups per Mole of CPA | qv* (Moles of water/mole of polar groups at Cv) |
|---|---|---|---|---|
| Acetamide | 4.1 | 2.4 | 2 | 1.2 |
| N-Methyl-Formamide | 3.9 | 2.6 | 2 | 1.3 |
| Acetol (hydroxy-acetone) | 3.6 | 2.8 | 2 | 1.4 |
| Ethylene glycol | 3.3 | 3.0 | 2 | 1.4 |
| 1,3-pro-panediol | 3.1 | 3.2 | 2 | 1.6 |
| 1,3-dihy-droxyacetone | ~2.0 | 5 | 3 | 1.7 | on qv*, should be the least toxic cryoprotectant of these six. In fact, 50% w/v acetamide is essentially non-toxic to kidney slices (Fahy, da Mouta, et al., in: Cell Biology of Trauma, C Oliver and J. J. Lemasters, eds, 1995), which is probably a record and is in marked contrast to the toxicity of 50% DMSO or 50% 1,2-propanediol. Other weak glass-formers of interest include acetoin [Cv>~60% w/w in water], hexafluoroacetone trihydrate, and related molecules.

"qv*=[(#moles of water)/(mole]/[(# polar groups)/(mole cryoprotectant)] or qv*=(#moles of water per unit volume or per unit mass of solution)/(# moles of polar groups on penetrating cryoprotectants per unit volume or unit mass of solution) at Cv".

The latter format follows from canceling out mole of cryoprotectant in the numerator and the denominator of the original formula, and mirrors the heading of column 5 of Table 1.

EXAMPLE 4

Viability Correlates with qv* in D(1)F-EG Solutions

Aqueous solutions of formamide alone do not vitrify (Fahy, in: Low Temperature Biotechnology: Emerging Applications and Engineering Contributions, J. J. McGrath and K. R. Diller, eds, ASME, 1988, pp. 113146), suggesting that formamide concentrations should be maximized. However, formamide also has specific toxicity that must be neutralized by the simultaneous presence of dimethyl sulfoxide (Fahy, da Mouta, et al., in: Cell Biology of Trauma, C. Oliver and J. J. Lemasters, eds, 1995), limiting how high the formamide concentration and the formamide to dimethyl sulfoxide (F:D) ratio can be.

Preliminary experiments showed that a) D(1)F vitrified at considerably lower concentrations than expected, and therefore that b) mixtures of D(1)F and the weak glass-former ethylene glycol in different proportions of EG:D(1)F up to 1:1 had the same or nearly the same Cvs. Initial toxicity trials were based on Cv values of 57–58% w/v, which were determined without filtering the solutions. When similar solutions were passed through a 0.22 micron filter, Cv tended to be lower (about 57% w/v).

Figure 4:
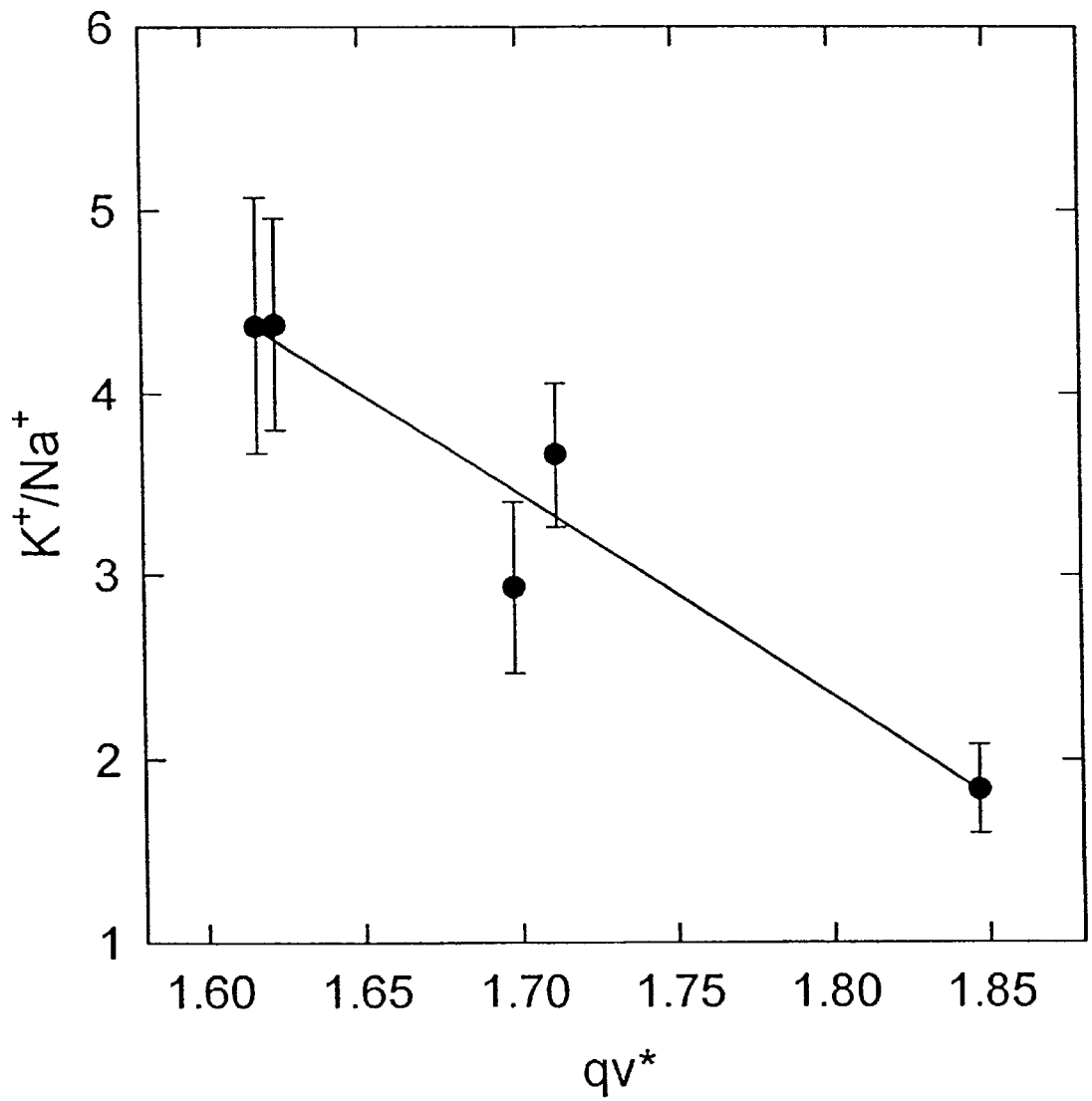
FIG. 4 shows the viability of rabbit renal cortical slices plotted against qv* in solutions containing a mixture of dimethyl sulfoxide (DMSO), formamide, and ethylene glycol (EG).

FIG. 4 shows the viability of rabbit renal cortical slices plotted against qv* in solutions containing a mixture of dimethyl sulfoxide (DMSO), formamide, and ethylene glycol (EG) in which the mole ratio of DMSO and formamide was kept fixed at 1:1 and this D(1)F mixture was mixed in varying proportions with EG (gram ratio of EG:D(1)F=0, 1:5, 1:4, 1:2, and 1:1). The solutions were at the total concentration needed to vitrify in each case; no polymer was present. As shown in FIG. 4, despite the uncertainties in Cv caused by lack of filtration, the toxicity of EG-D(1)F mixtures was once more consistent with the ranking of these mixtures according to qv*. This was true even though the solutions in FIG. 2 (only vitrifiable at 1,000 atm; all contain polymer) were substantially different from those in FIG. 4 (all vitrify at 1 atm, none contain polymer). Mixtures having EG:D(l)F weight ratios of 1:1 and 1:2 had near-equivalent qv* values of around 1.62 (because the 1:2 solution had a measured Cv of 58% w/v, vs. 57% w/v for the 1:1 solution), and produced identical slice toxicities at this qv* value (FIG. 4) despite large differences between the compositions of these mixtures.

FIG. 5 shows an interesting comparison between the toxicity of the solutions and the absolute concentrations of DMSO, formamide, and EG that are simultaneously present in each case. It shows the data of FIG. 3 plotted in terms of the absolute concentrations of DMSO, formamide, and ethylene glycol in the solutions, as well as in relation to the mole percentage of D(1)F in the mixture. Toxicity at ratios of 0, 1:5, and 1:4 (qv*=1.85, 1.7, and 1.74, respectively) was associated with concentrations of formamide too high to be neutralized properly by DMSO (Fahy, da Mouta, et al., in: Cell Biology of Trauma, C. Oliver and J. J. Lemasters, eds, 1995), while concentrations of up to nearly 30% w/v EG were not overtly harmful. FIG. 5 indicates that the limit for an acceptable mole fraction of D(1)F/(D(1)F+EG) is below 0.8 and above 0.67 for a total concentration of 57–58% w/v D(1)F, and that a concentration of about 14% formamide is the maximum that is associated with minimal injury.

EXAMPLE 5

Viability Correlates with q* in Modified VS41A

VS41A was the best solution previously known to us, so it was of interest to compare it to solutions of lower qv*. VS41A contains about 38.2% w/v D(1)F, or almost exactly 14% formamide, the maximum amount found compatible with high viability in Example 4. The other component of VS41A is 1,2-propanediol (PG), which is an excellent glass former (qv* about 2.6), and is a far better glass former than D(1)F, which is why it has been a major component of VS41A and predecessor solutions to it since about 1983. But according to the new theory, this component should be replaced, as much as possible, with a weaker glass-forming component. Ethylene glycol was therefore selected as a known weak glass-forming agent, and the PG in VS41A was replaced gram for gram with EG (forming a solution named Veg) to gain a further evaluation of the theory. Even though this modification was expected to lower the Cv of the solution, all attempted one-to-one replacement experiments in the past have failed to attain reductions in toxicity (see, e.g., Fahy, Cryobiology 35: 344–345, 1997). In the current test, however, this rule was broken, as indicated in Table 2.

TABLE 2

Comparison[1] of VS41A with Veg and VS4

|  | VS41A | Veg |
| --- | --- | --- |
| Concentration | 55% w/v | 55% w/v |
| Concentration | 8.41M | 8.91M |
| Density | 1.067 | 1.067 |
| Moles of water per liter | 26.3 | 26.3 |
| qv* | 1.92 | <1.74 |
| K+/Na+ (mean ± sem) | 4.93 ± 0.15 | 7.17 ± 0.15 |
| As fraction of controls | 59.8% | 87.0% |

[1]Toxicities of vitrification solutions can best be compared based on q* at the q* needed to vitrify, or qv*

The results shown in Table 2 were surprising and informative in several respects. In the first sense, they allowed the specific contribution of the PG in VS41A to be identified as the cause of nearly three-quarters of the toxicity of VS41A. Second, they showed that a solution that is more concentrated than VS41A (on a molar basis) can have only about one-fourth the toxicity of VS41A about a 10% vs. about a 60%.

EXAMPLE 6

Acceptable Limits of PG in Veg-like Solutions

Figure 6:
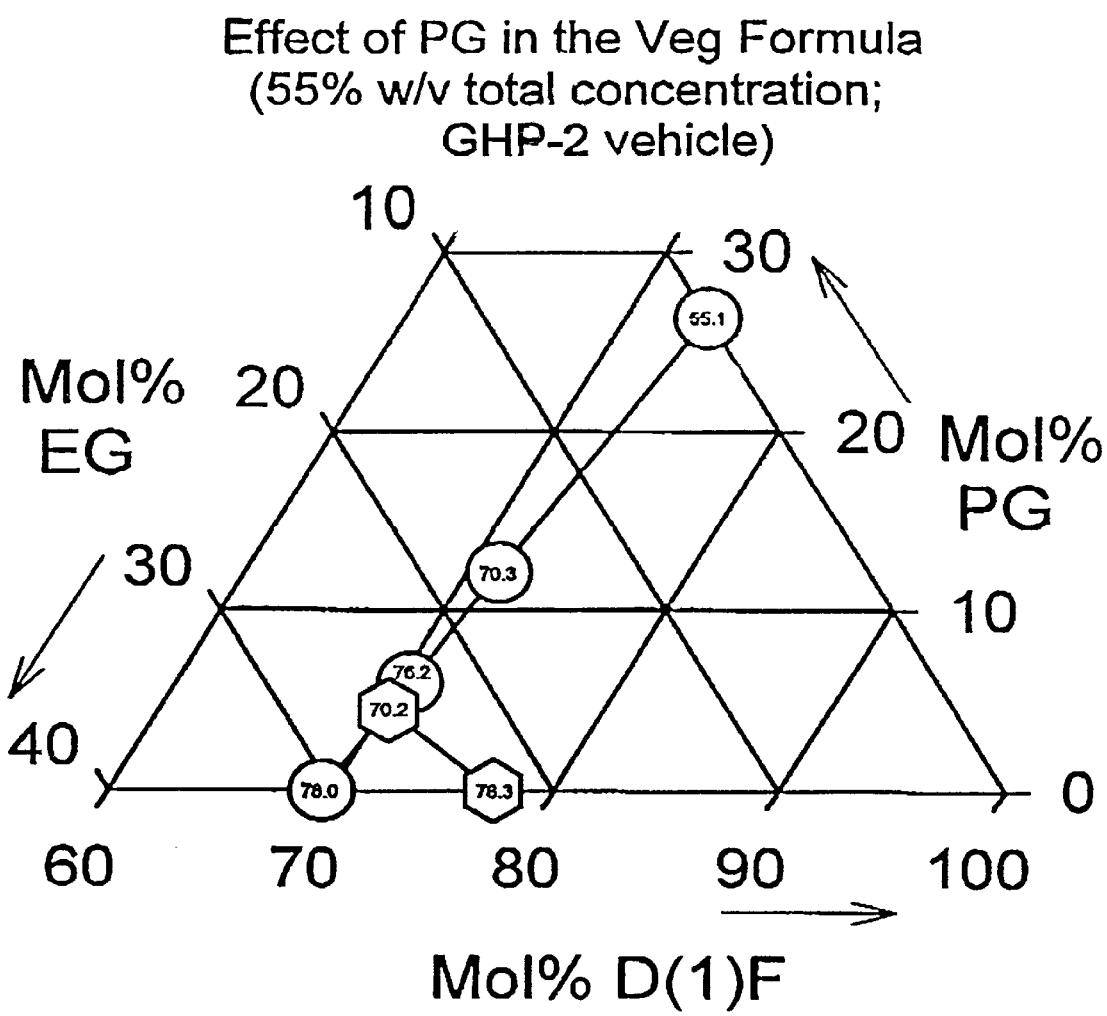
FIG. 6 shows the effect of varying Veg by a) increasing the D(1)F:EG mole ratio and by b) systematically replacing EG with PG.

FIG. 6 presents a map of how the balance between EG, D(1)F, and PG affects the viability of rabbit renal cortical slices when total concentration is held fixed at 55% w/v. It shows the effect of varying Veg by a) increasing the D(1)F:EG mole ratio and by b) systematically replacing EG with PG. The numbers within the points indicate the percent of untreated control K/Na ratio achieved after exposure to the composition defined by the ternary composition triangle (percent of control calculated without correction for background K/Na >0). As can be seen from two separate experiments (circles and hexagons, respectively), progressive replacement of the EG of Veg (point at 70 mol % D(1)F, 30 mol % EG, 0 mol % PG) with PG to form solutions more like VS41A (point at about 73 mol % D(1)F, 27 mol % PG, and 0 mol % EG) monotonically reduces viability from the 78% seen for Veg in GHP-2 to the 55% viability seen for VS41A. However, the drop is only to 70–76% viability when 3–4% w/v EG is replaced with 3–4% w/v PG (points near 4 mol % and 6 mol % PG), which may be an acceptable tradeoff to accept in exchange for enhanced solution resistance to devitrification and for enhanced vitrification tendency, in some circumstances. Even replacing 8% W/v EG with 8% w/v PG (point near 12 mol % PG) is still consistent with a viability of 70% of untreated control slice K/Na, again indicating that the majority of injury associated with the use of PG occurs when more than 8% PG is present.

FIG. 6 also shows that a D(1)F:EG mol % of up to 77 is feasible without a loss of viability. This is consistent with but further defines the result provided in FIG. 5B.

EXAMPLE 7

Acceptable Variations of Veg

Figure 7:
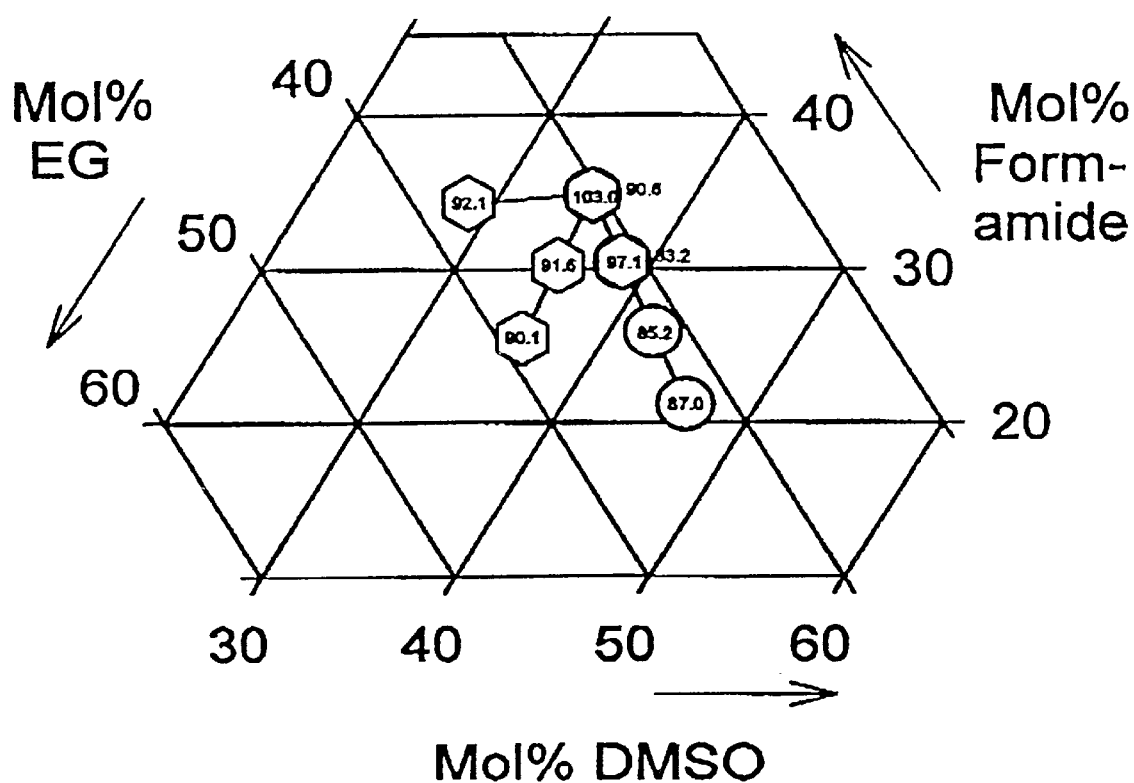
FIG. 7 shows the effect of varying Veg by reducing formamide in favor of DMSO or in favor of ethylene glycol, or by reducing DMSO in favor of ethylene glycol.

FIG. 7 shows the effect of varying Veg by reducing formamide in favor of DMSO or in favor of ethylene glycol, or by reducing DMSO in favor of ethylene glycol, indicating that variations within these limits maintain Veg in a range of high viability. FIG. 7 is in the same format as FIG. 6, except that no PG is involved and variations in the D:F ratio are included. The point yielding 90.6–103% of control function represents Veg. Veg was varied in three directions: formamide was progressively replaced with DMSO (line descending to the right); formamide was progressively replaced with EG (line descending to the left); and DMSO was lowered in favor of EG (line proceeding horizontally to the left). As indicated in the figure, all three variations tended to worsen the K/Na ratio, implying that the formula for Veg is nearly optimum, but all of the variant data points remain far superior to VS41A, and hence all are acceptable variants within the scope of the invention. As noted above, raising formamide is expected to result in increased injury, so the only other possibility for improving the formula for Veg (other than by including other agents) is to increase the amount of DMSO in the solution at the expense of ethylene glycol. Information bearing on this question is given below.

EXAMPLE 8

Amide Universality and Superior Devitrification Resistance

Figure 8:
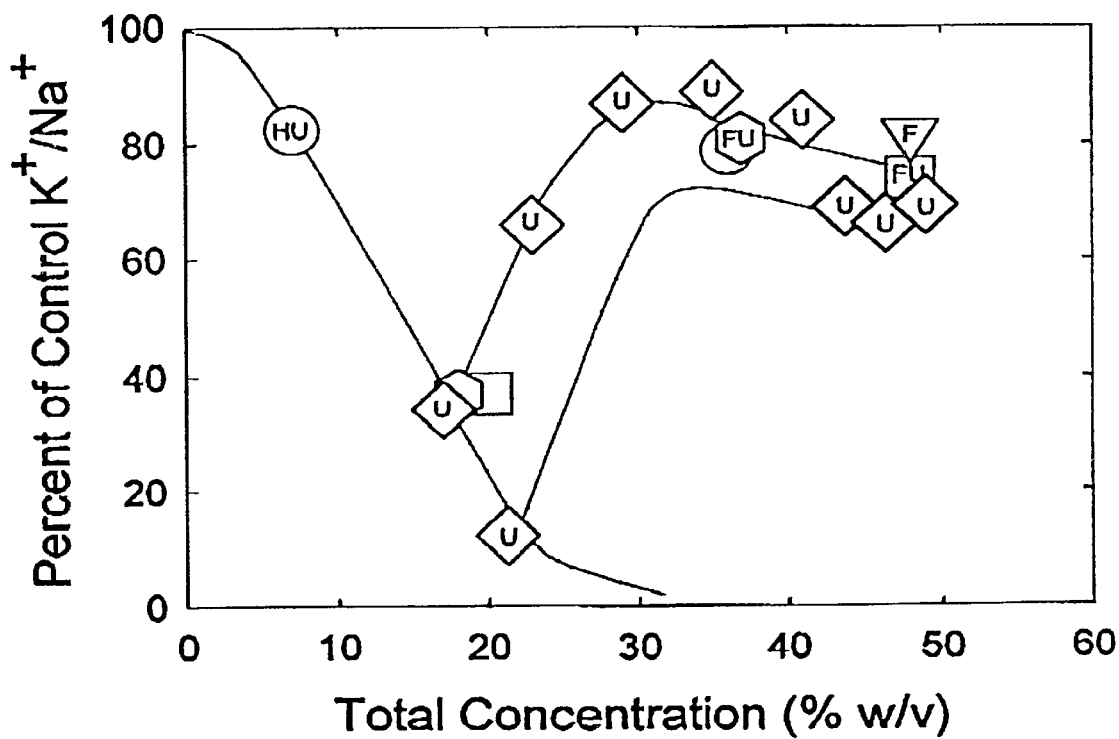
FIG. 8 describes the universality of formamide, urea, formamide/urea mixtures, and hydroxyurea in terms of their effects on cell viability and in terms of the neutralization of these effects by dimethyl sulfoxide.

FIG. 8 collects data on the toxic effect of amides and amide mixtures on rabbit renal cortex and the reversal of these toxic effects by DMSO. It describes the universality of formamide, urea, formamide/urea mixtures, and hydroxyurea in terms of their effects on cell viability and in terms of the neutralization of these effects by dimethyl sulfoxide. These data extend prior data (Fahy, da Mouta, Tsonev, Khirabadi, Mehl, and Meryman, in: Cell Biology of Trauma, J. J. Lemasters and C. Oliver, eds., CRC Press, 1995, pp. 333–356) to a surprising degree, as follows. First, hydroxyurea, urea, and equal weights of urea and formamide (circles, diamonds, and hexagons, respectively, on the descending curve) appear to have the same toxic effect as formamide alone on a percent weight/volume basis. This is true despite variations in molecular mass between these amides, despite the fact that urea and hydroxyurea have two amino groups vs. the one amino group of formamide, and despite the fact that one of the amino groups of hydroxyurea is modified with a hydroxyl group. Second, the neutralization of the toxicity of all these agents and agent combinations by the addition of DMSO (curves rising to the right) also seems to follow the same quantitative trends in terms of % w/v concentrations documented previously for the neutralization of formamide toxicity alone (inverted triangle; and Fahy, da Mouta, Tsonev, Khirabadi, Mehl, and Meryman, in: Cell Biology of Trauma, J. J. Lemasters and C. Oliver, eds., CRC Press, 1995, pp. 333–356), again despite the differences just noted.

Like formamide, there may be an upper limit on the amount of urea or other amide whose toxicity can be reversed by DMSO. However, a urea concentration in the vicinity of 15% should be essentially fully detoxifiable, and may have advantages, because urea forms even more poorly glass-forming solutions than does formamide (point 6 of FIG. 3). Furthermore, when these urea-rich solutions vitrify, they fail to devitrify on warming, a remarkable and unexpected property presumably due to depletion of water from the solution to such an extent that insufficient water remains to freeze. Advantageous compositions containing urea are given in and implied by the master vitrification solution table (see below).

The flexibility provided by FIG. 8 should allow investigators to tailor their amide mix according to peculiarities of cell membrane permeability and biochemical toxicity that vary between these amides and amide mixes. Hydroxyurea, which is known as an inhibitor of cell division, had no adverse effect in the experiments depicted in FIG. 8, and will be advantageous, for example, when cell division is undesirable.

EXAMPLE 9

Formulae for Preservation by Supercooling

Figure 9:
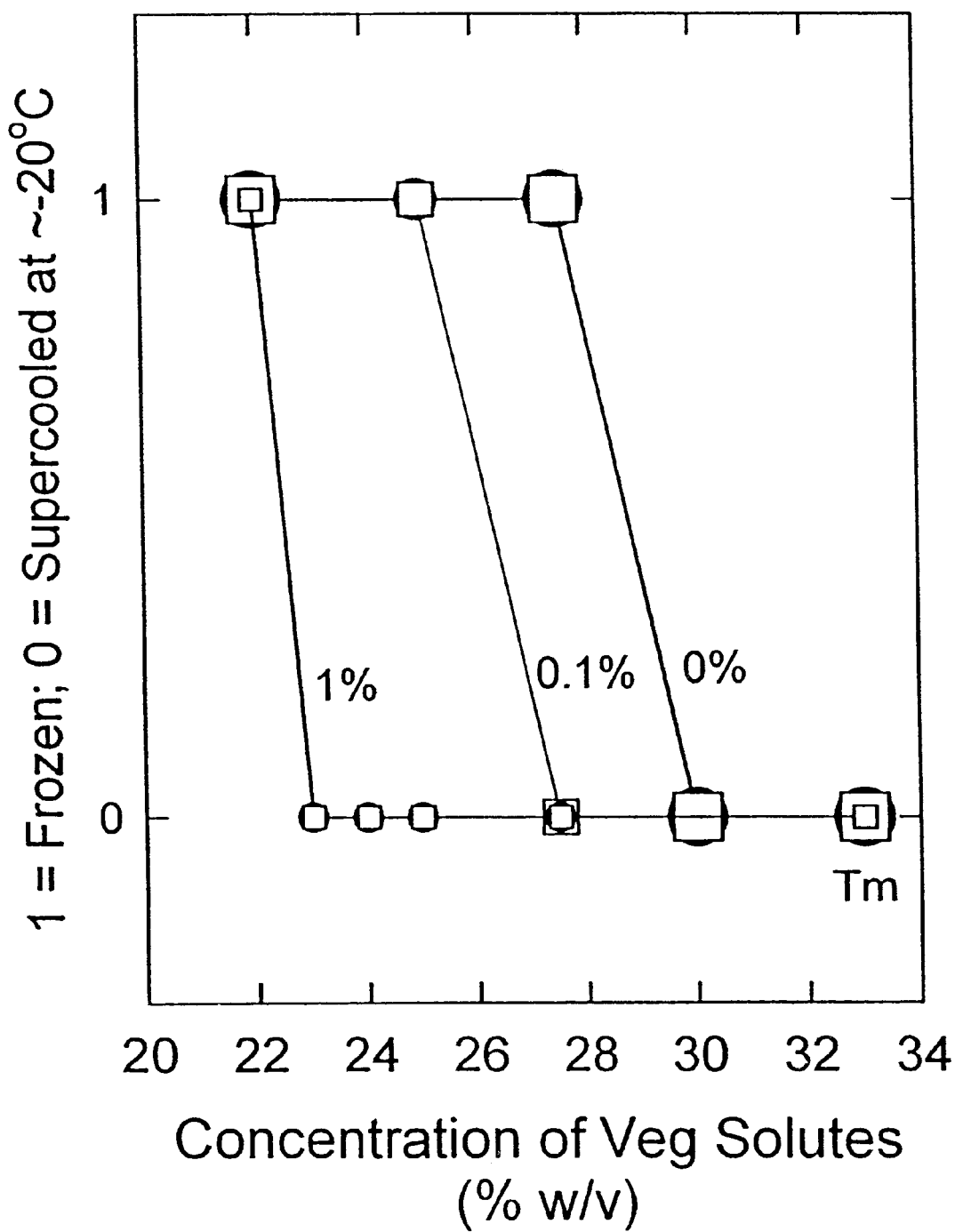
FIG. 9 illustrates the process for selecting solutions for use in supercooling experiments on living systems.

FIG. 9 illustrates the process for selecting solutions for use in supercooling experiments on living systems. FIG. 9 graphically depicts the concentrations of Veg solutes needed, in the absence and in the presence of 0.1–1.0% PVA of molecular mass ~1,000 daltons (a forthcoming commercial product called "X-1000"), to establish stable supercooling for at least 48 hours in a household refrigerator freezer compartment, the most practically-available temperature for supercooled storage. The circles represent solutions containing the physiological solution RPS-2, which is described in the literature, and squares represent solutions based on a vehicle called RPS-T, wherein 175 mM trehalose plus 5 mM glucose replace the 180 mM glucose concentration found in RPS-2.

TABLE 3

Carrier (Vehicle) Solutions Used in These Studies

|  | FW | RPS-2 (mM) | Euro-Collins (mM) | MHP-2 (mM) | GHP-2 (mM) |
| --- | --- | --- | --- | --- | --- |
| adenine hydrochloride | 171.6 | 1 | — | 0.94 | 1 |
| adenosine | 267.2 | — | — | — | — |
| calcium chloride | 111 | 1 | — | 1 | — |
| glucose | 180.2 | 180 | 194 | 5 | 175 |
| glutathione, reduced | 307.3 | 5 | — | 3 | 3 |
| Heparin | — | — | — | 1000 IU/L | 1000 IU/L |
| hydroxyethyl starch | 500K | — | — | 50 g/L | — |
| magnesium chloride, hexahydrate | 203.3 | 2 | — | 1 | — |
| magnesium sulfate, heptahydrate | 246.5 | — | — | — | — |
| mannitol | 182.2 | — | — | 170 | — |
| potassium chloride | 74.55 | 28.5 | 15 | — | — |
| potassium gluconate | 234.2 | — | — | — | — |
| potassium phosphate, dibasic | 174.2 | — | 42 | — | — |
| potassium phosphate, monobasic | 136.1 | 7.2 | 15 | — | — |
| ribose (D-) | 150.1 | — | — | 0.94 | 0.94 |
| sodium acetate, trihydrate | 136.1 | — | — | — | — |
| sodium bicarbonate | 84.01 | 10 | 10 | 10 | 10 |
| sodium chloride | 58.44 | — | — | — | — |
| sodium HEPES | 260.3 | — | — | 15 | 15 |

As shown, Veg solutes in either vehicle solution remain liquid at a total concentration of 33% w/v and 30% w/v under such conditions (temperature about −20° C. +/−3 degrees), but solutions at a concentration of 27.5% freeze spontaneously, so the safe concentration for supercooling is about 28–30% w/v, or perhaps 29%. The equilibrium concentration of Veg solutes required to depress the freezing point to the average temperature in the aforementioned freezer is approximately 33–34% w/v, meaning that Veg solutions in either vehicle solution will supercool if their concentrations are reduced by about 5–6% w/v, but no further. Addition of 0.1% X-1000 to 27.5% Veg solute solutions eliminates freezing of 27.5% solutions, but not of 25% w/v Veg solutions. However, addition of 1% X-1000 depresses the concentration needed to supercool down to 23% w/v, although freezing still takes place at a Veg solute concentration of 22% w/v. Thus, 1% X-1000 extends the range of accessible concentrations for short term storage (for example, for 48 hr) in low-toxicity media from the initial 5–6° C. to a total concentration depression of 10° C., or about double the normal margin. Hence, one method for storing systems in low-toxicity media under conditions of supercooling is to a) determine the desired storage temperature, b) determine the concentration of cryoprotectant that has that temperature as its equilibrium melting point, c) subtract about 8–10% w/v from that equilibrium concentration, and d) store the system of interest at the storage temperature of interest in the thus-calculated solution of interest. If desired, higher concentrations of PVA can be used for still greater supercooling protection.

One caution is that it is essential to ensure full permeation of the PVA into the sample prior to cooling, and agitation of the sample should be minimized during storage. In preliminary experiments, some test tissue slices froze due to incomplete penetration of PVA into the inadequately exposed slices.

EXAMPLE 10

Veg Solutes Form Superior Freezing Solutions

A recent freezing experiment compared freezing of rabbit kidney slices to −130° C. in the presence of either 30% w/v DMSO or 30% w/v Veg solutes. The K/Na ratio after freezing and thawing in DMSO was 2.46+/−0.30, whereas the K/Na ratio after freezing and thawing in 30% w/v Veg solutes was 3.10+/−0.07 ($p<0.05$).

A recent freezing experiment compared freezing of rat hepatocytes in suspension to −140° C. in the presence of either 10% v/v DMSO or 10% v/v Veg solutes. Relative to the initial viability, 98% of the Veg-treated, non-frozen hepatocytes were able to exclude trypan blue dye, whereas only 70% of the DMSO-treated, non-frozen hepatocytes retained their dye exclusion capability after addition and removal of DMSO alone. After freezing and thawing, 65% of the initial number of freshly isolated hepatocytes remained capable of excluding trypan blue dye, whereas only 60% of frozen-thawed hepatocytes retained this ability when frozen with DMSO.

Human sperm was exposed to 2 M Veg solutes or 2 M glycerol near 0° C. using gradual addition methods, then frozen, thawed, and videotaped without removing the cryoprotectant. The human sperm frozen in 2 M Veg recovered motility similar to that observed prior to addition of Veg, whereas sperm frozen in 2 M glycerol was largely quiescent upon thawing.

EXAMPLE 11

Veg-Type Vitrification Solutions Permit Superior Recovery after Vitrification and Rewarming Rabbit renal cortical slices were equilibrated with one of three vitrification solutions, then vitrified, rewarmed, and evaluated for K/Na ratio after 90 min of recovery at 25° C. The results were as shown in Table 4.

TABLE 4

K/Na ratio of rabbit renal cortical slices

| Solution | K/Na − 0.31* | Comparison to VS41A |
|---|---|---|
| VS41A | 1.66 +/− 0.105 | — |
| Veg − 4% D(1)F + 4% PVP K30 + 3% acetol | 2.76 +/− 0.144 | p < 0.05 |
| Veg − 4% D(1)F + 7% PVP K30 | 3.03 +/− 0.206 | p < 0.05 |

*0.31 is the K/Na ratio of completely dead slices, and is equal to the K/Na ratio of the bathing medium.

EXAMPLE 12

Veg-Type Vitrification Solutions are Less Toxic to Human Corneas than is VS41A

Hepatocytes retained their dye exclusion capability after addition and removal of DMSO alone. After freezing and thawing, 65% of the initial number of freshly isolated hepatocytes remained capable of excluding trypan blue dye when frozen with 10% v/v Veg solutes, whereas only 60% of frozen-thawed hepatocytes retained this ability when frozen with DMSO.

EXAMPLE 13

VS41A is Superior to Prior Art Vitrification Solutions, but Veg is Superior to VS41A The assumption that no prior art solution is better than VS41A was validated by preparing three solutions described in the literature that a) were claimed to yield high survival rates in the systems for which they were used, and b) appeared more likely than other solutions in the literature to have low toxicity based on their similarity to Veg. These 3 solutions were compared to VS41A and to Veg, and the results are shown in Table 5.

TABLE 5

Comparison of previously used cryoprotectant solutions to VS41A and Veg

| Solution | VS41A | EFS | EGP | EPT | Veg |
|---|---|---|---|---|---|
| K/Na − .31 | 3.00 | 2.92 | 2.82 | 1.69 | 4.41 |
| SEM | 0.10 | 0.09 | 0.14 | 0.07 | 0.13 |

Abbreviations:
EFS = 40% v/v EG + 18% Ficol (70 kD) + 0.3 M sucrose
EGP = 8.5 M EG + 10% PVP
EPT = 40% v/v EG + 20% PVP + 11.3% trehalose Steps for introducing and removing the vitrification solutions: ⅛th of full strength; ¼th of full strength; one-half of full strength; full strength (1X) vitrification solution; ½X+300 mM mannitol; ⅜X +300 mM mannitol; ¼X+300 mM mannitol; 0X+300 mM mannitol; ordinary vehicle (MHP-2). Each step is 20 min except for 1X step, which is 40 min. All steps done at 0° C.

EXAMPLE 14

Many Variations of Veg are Superior to VS41A

Table 6, which follows, lists solutions found to be advantageous within the present invention. The listing includes the identity of the solution, the viability result associated with the solution in relation to exposure to other solutions or in relation to untreated controls, and information concerning the vitrification tendency and devitrification tendency of the solution. Further variations will be apparent to those of skill in the art upon contemplation of the exemplary solutions listed.

Further perspective on the value of the solutions listed in Table 6 can be obtained by considering one early example, Veg+3% EG (solution #15-1). This solution has toxicity similar to that of a solution known as V52, but Veg+3% EG, unlike V52, is very possibly sufficiently stable for vitrification of rabbit kidneys. V52 is a composition halfway between VS4 and VS41A, and has been used to perfuse rabbit kidneys to the point of osmotic equilibration, cool them −32° C., warm them back up, and recover them after transplantation with immediate contralateral nephrectomy with attainment of a 100% survival rate and a 100% return of the recipient rabbits to a permanently normal clinical state (Khirabadi et al., Cryobiology 31: 597, 1994). If Veg+3% EG can achieve the same result in terms of toxicity, it may then be sufficiently stable to go on to successfully bank these kidneys at cryogenic temperatures by vitrification. And Veg+3% EG is far from the most superior or advantageous solution listed in Table 6. It should be clear from this perspective that even apparently small gains in toxicity can be crucial to the success of a cryopreservation process, and that solutions ranked at least as low as solution 15-1 could be of great value.

Figure 10:
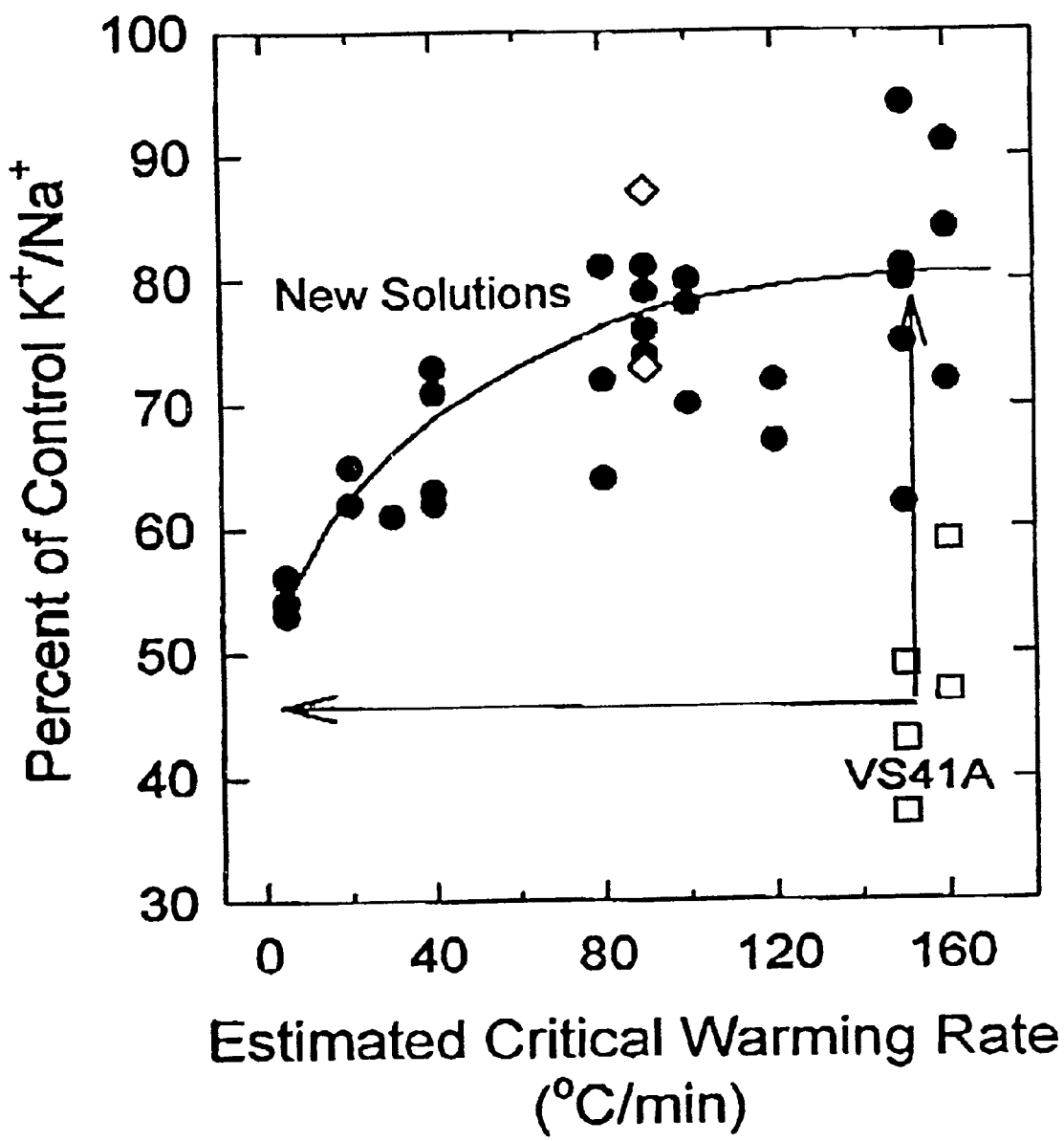
FIG. 10 summarizes the gain in stability and the gain in viability attained by the new solutions in comparison to the former standard solution, VS41A.

Additional perspective is provided in FIG. 10, in which the data of Table 6 are converted into a rough estimate of the viability vs. critical warming rate (to prevent serious devitrification on warming)curve. VS41A (open boxes) is estimated to require heating at about 150–160° C./min in these experiments, depending on the vehicle or carrier solution used. Solutions of the invention, at the same estimated critical heating rate, provide about double the viability permitted by VS41A (vertical arrow near "VS41A" label). Looked at differently, if the viability provided by VS41A is considered satisfactory, the solutions of the invention can provide the same viability but at a critical warming rate about 100 times lower than the critical rate needed for VS41A. The experimental variability of the data is suggested by the diamonds, which depict two independent tests (34-4 and 36-1) of the same solution.

There has not been sufficient time, as of the submission of this application, to analyze the data of Table 6 in terms of qv*. However, it is apparent that exceptions will be found to the qv* rule. Apparently, small concentration increments (circa 3% w/v) generally have similar effects on viability in a Veg background. This permits the stability of the solution to be enhanced by good glass-forming agents such as methoxyglycerol without penalties, provided the other rules of solution manufacture are adhered to. This is an important extension of the use of the qv* method.

By the same token, agents such as acetol, 1,3-propanediol, dihydroxyacetone, and acetoin are not able to replace ethylene glycol entirely in Veg, perhaps because these agents are too hydrophobic. Use in moderation, however, can be advantageous.

The vitrification data reported in Table 6 were obtained as follows. Samples were tested by affixing at least one test tube containing 5 ml of sample plus 1 ml of isopentane as a surface layer to a rigid support and attaching this support a fixed distance over the surface of liquid nitrogen in a medium-necked dewar, with one parallel sample of the same solution being run concurrently to document the thermal history of the sample, and were scored based upon their appearance after cooling or based upon their solubility. The scores were considered reliable only for the samples riot containing thermocouple probes. All samples contained a biologically compatible vehicle or carrier solution. After cooling and scoring were complete, samples were also examined where applicable for stability on warming. This was accomplished by transferring the sample and reference tubes into either a) a bath of approx. 100 ml of methanol at approximately room temperature (estimated warming rate, 60–100 degrees/min), or b) a boiling or near-boiling water bath (estimated warming rate, 100–200 degrees/min or more), or in some cases in other ways. For example, in some cases samples were transferred to a methanol bath held at 0° C., and in others samples were cooled and warmed in a controlled rate freezer to witness freezing on cooling or on warming at relatively slow rates of temperature change. Cooling curves, and hence calculated average cooling rates (9–11 ° C./min) were very consistent. Warming rates as calculated were found to be somewhat inconsistent. This may be due to the high speed of warming compared to the speed of cooling, uncontrollability of the exact position of the temperature probe between the wall and center of the sample, imperfect consistency of stirring speed or manual agitation speed in the warming bath, and imperfect consistency of the warming bath temperature and of the sample temperature at the time the sample was transferred to the warming bath (usually −105 to −95° C., sometimes as low as around −110° C.) as well as differences from sample to sample in the thermal properties of the samples themselves.

TABLE 6

Exemplary Low-Toxicity Cryoprotectant Solutions

| Ref. No. | Soln Description | % K+/Na+ | cf'd to: | Aprx crit CR* | Devit: ~150°/ minute | Devit: ~80°/ minute | Devit: (crit. WR) | Data source |
|---|---|---|---|---|---|---|---|---|
| 22-REF | VS41A in Euro Collins Solution (EC) | 43 | EC | 10 | NDV | Fr (T) | Nt | 8-8-98 run |
| 22-1 | Veg + 5% acetol (90% pure) (EC) | 54 | EC | ≦2–5 | Nt | Nt | (<10) | NOTES |
| 22-2 | Veg + 5% MG (3-methoxy-1,2-propanediol) (EC) | 53 | EC | ≦2–5 | Nt | Nt | (<10) | NOTES |
| 22-3 | Veg + 2% sucrose + 2% PVA 9.5 k (in RPS-2) | 56 | RPS-2 | ≦2–5 | Nt | Nt | (<10) | NOTES |
| 27-1 | Veg − 3% Veg + 7% PVP 40000 (MHP2) | 61 | MHP-2 | 10 | Nt | Nt | ~30 | BW, est. |
| 27-2 | Veg − 3% Veg + 6% PVP 5000 + 1% PVA 7000 | 62 | MHP-2 | 10 | nt | nt | ~20 | BW, est |
| 27-3 | Veg − 5% Veg + 4% PVP 5000 + 4% PEG 1000 + 1% PVA 7000 | 62 | MHP-2 | 10 | Nt | Nt | ~20 | BW |
| 27-4 | Veg − 5% Veg + 8% PVP 5K + 1% PVA 7000 (in MHP-2) | 65 | MHP-2 | 10 | Nt | Nt | ~20 | BW |
| 23-REF | VS41A in RPS-2 | 47 | RPS-2 | 10 | NDV | Fre | Nt | est., 22 REF |
| 23-1 | Veg + 3% acetamide in RPS-2 | 62 | RPS-2 | 10 | NDV | ~NDV | <~40 | 170, 180, 181 |

TABLE 6-continued

Exemplary Low-Toxicity Cryoprotectant Solutions

| Ref. No. | Soln Description | Aprx % K+/Na+ | cf'd to: | crit CR* | Devit: ~150° / minute | Devit: ~80° / minute | Devit: (crit. WR) | Data source |
|---|---|---|---|---|---|---|---|---|
| 23-2 | Veg + 3 MG (in RPS-2) | 63 | RPS-2 | 10 | NDV | ~NDV | <~40 | 171, 184 |
| 23-3 | Veg + 3% PVP 40,000 (in RPS-2) | 71 | RPS-2 | 10 | NDV | ~NDV | <~40 | 164, 167, 183 |
| 23-4 | Veg – 4% D(1)F + 4% PVP 40,000 + 3% MG (in RPS-2) | 73 | RPS-2 | 10 | NDV | nt | <~40 | 173, 185 |
| 54-1 | Veg + 1% DMSO + 1% PVA 1000 80% hydrolyzed in RPS-T | 72 | RPS-2 | 10 | Nt | NDV | Nt | NKT.56 |
| 54-4 | Veg + 2% DMSO in RPS-T | 79 | RPS-2 | 10 | nt | ~NDV | nt | NKT.56 |
| 54-3 | Veg + 1% DMSO + 1% PVA 1000 in RPS-2 | 76 | RPS-2 | >10 | nt | ~NDV | nt | NKT.56 |
| 54-5 | Veg + 1% PVA 1000 in RPST | 81 | RPS-2 | 10 e | nt | ~NDV | nt | 54-2 |
| 54-2 | Veg + 1% PVA 1000 in RPS2 | 72 | RPS-2 | 10 | nt | SDV | nt | NKT-56 |
| 42-2 | Veg – 4% D(1)F + 5% EG + 1% PVA 1000 (aldehydes reduced) | 74 | GHP2 | 10 | nt | ~NDV | nt | NKT.VIT |
| 42-5 | Veg + 1% EG + 1% PVA 1000 (red'd) | 80 | GHP2 | 10 | nt | wsDV | nt | 438 |
| 24-REF | VS41A in MHP-2 | 37 | MHP2 | 10 | NDV | PDV to ~NDV | Fr (10) | 218, 219, 230 |
| 24-1 | Veg – 4% D(1)F + 4% PVP 40,000 + 2.7% acetol | 62 | MHP2 | 10 | NDV | Fr (ST) | nt | 18 |
| 24-2 | Veg – 4% D(1)F + 7% PVP 40,000 in MHP-2 | 67 | MHP2 | >10 | NDV | sDV | nt | E4.4, NKT23 |
| 25-REF | VS41A in MHP-2 | 49 | MHP2 | 10 | NDV | PDV to ~NDV | Fr (at 10°/min) | 218, 219, 230 |
| 25-1 | Veg – 4% EG + 7% PVP 40,000 in MHP-2 | 72 | MHP2 | ~10e | NDVe | nt | nt | 19-1 |
| 34-1 | 58.5% D(1)UE$_{20}$ + 6% PVP 5000 | 64 | GHP-2 | 10 | nt | NDV | Nt | NKT1, 28 |
| 34-2 | Veg – 4% D(1)F + 5% PVP 5000 + 1% PVA 7000 (GHP2) | 78 | GHP2 | 10 | Nt | wsDV | nt | NK + b1vit. 46 |
| 34-3 | 55% E [D(0.7)F]$_{38.18}$ + 6% PVP 5000 | 81 | GHP2 | 10 | nt | NDV | nt | NKT1 & 30 |
| 34-4 | 53% E [D(0.7)F]$_{38.18}$ + 5% PVP 5000 + 1% PVA 7000 in GHP-2 | 87 | GHP2 | 10 | nt | ~NDV | nt | NKT1 & 31 |
| 36-1 | Same as 34-4 | 73 | GHP2 | 10 | nt | ~NDV | nt | NKT1 & 31 |
| 36-2 | 53% E [D(0.7)F]$_{40}$ + 5% PVP 5000 + 1% PVA 7000 | 73 | GHP2 | 10 | nt | ~NDV | nt | NKT2, 37 |
| 39-1 | Same as 34-2 | 70 | GHP2 | 10 | nt | wsDV | nt | NK + blvit. 46 |
| 39-2 | Veg – 4% D(1)F + 5% PVP 5000 + 1% PVA 1000 80% hydrol'd | 75 | GHP2 | 10e | nt | VWSD Ve | Fr | 34-2 |
| 39-3 | Veg – 4% D(1)F + 5.5% PVP 5000 + 0.5% PVA 1000 80% hydrol'd | 69 | GHP2 | 10e | nt | WSDV e | Fr | 39-2, 34-2 |
| 20-REF | VS41A in RPS-2 | 59 | RPS-2 | 10e | NDVe | Fre | nt | VS41A/E C/Etc |
| 20-1 | Veg + 1% EG + 0.1% PVA 9500 | 81 | RPS-2 | 10 | NDV | Fr | nt | 19 |
| 19-1 | Veg – 4% EG + 7% PVP 40K | 94 | 17-3 | >10 | NDV | nt | nt | (E4.4) |
| 17-3 | Veg – 4% D(1)F + 7% PVP 40,000 (40K) | 91 | RPS-2 | >10 | NDVe | SDVe | ~40e | NKT23 E4 |
| 18-1 | Veg – 4% D(1)F + 7% pluronic F68 in RPS-2 | 80 | RPS-2 | 10 | NDV | nt | nt | |
| 18-2 | Veg + 1% 1,4-butanediol | 75 | RPS-2 | ≧10 | NDV | Fr | nt | 15 |
| 18-4 | Veg – 4% D(1)F + 7% PVP 40,000 | 84 | RPS-2 | >10 | NDVe | SDVe | ~40e | NKT23, E 4 |
| 18-REF | Veg (Reference only) | 85 | RPS-2 | NA | NA | NA | NA | NA |

TABLE 6-continued

Exemplary Low-Toxicity Cryoprotectant Solutions

| Ref. No. | Soln Description | % $K^+/Na^+$ | cf'd to: | Aprx crit CR* | Devit: ~150°/ minute | Devit: ~80°/ minute | Devit: (crit. WR) | Data source |
|---|---|---|---|---|---|---|---|---|
| 15-1 | Veg + 3% EG (in RPS-2) | 126 | VS41A | >10 | NDV | Fr | nt | E4.4, Table 13 |
| 15-3 | Veg + 1% 1,3-propanediol | 136 | VS41A | 10 | ~NDV | Fr | nt | E4.4 |

Abbreviations: E or EG = Ethylene glycol; D = DMSO; F = formamide; U = urea; D(n)Y = DMSO in an n:1 mole ratio of D to Y, where Y is another cryoprotectant; subscripted numbers, such as E20 or [D(.7)F]40, refer to absolute numbers of grams per deciliter of the substance preceeding the subcript, such as ethylene glycol or D(.7)F, respectively; MG = 3-methoxy-1,2-propanediol; PVP - polyvinyl pyrrolidone; PEG = polyethylene glycol; PVA = polyvinyl alcohol, 80% hydrolyzed from polyvinylacetate; NDV = no devitrification; Fr = Froze T = transparent ice only; pDV = partial devitrification; sDV = surface devitrification only (devitrification at the receding liquid/rubbery phase boundary only); wsDV = weak surface devitrification; ~ = approximately; nt = not tested; e = estimated; % $K^+/Na^+$ represents a comparison between two groups of rabbit renal cortical slices containing usually 8–12 slices each. *Approximate cooling rate required for complete visual vitrification. Low-ref no. RPS-2 data may overextimate the stability on cooling and warming of the CPA solution in RPS-2. Standard method of introducing and removing CPA and of testing for $K^+/Na^+$ ratios corrected by subtracting 0.309 from the original ratios to correct for non-zero backgrounds.
crit. WR = the critical warming rate that is just sufficient to prevent freezing (devitrification), Soln = solution, Fr (10) = Froze at a warming rate of 10° C./min.

Other variations in both solutions and in the finer aspects of calculating qv* will be apparent to those of skill in the art.

What is claimed is:

1. A cryoprotectant solution comprising: dimethyl sulfoxide, an amide selected from the group consisting of formamide, urea, acetamide, hydroxyurea and N-methyl formamide, and ethylene glycol or ethylene glycol in combination with propylene glycol wherein the propylene glycol replaces less than 8% w/v of the ethylene glycol.

2. The cryoprotectant solution of claim 1, further comprising: a polymeric material selected from the group consisting of: ficol, polyethylene glycol, polyvinylpyrrolidone, and polyvinyl alcohol, said polymeric material ranging from about 800 daltons to about 5,000 daltons as a non-penetrating agent for facilitating vitrification and inhibiting devitrification in vitrification solutions, wherein said polymeric material is hydrophillic and nontoxic.

3. The cryoprotectant solution of claim 2, wherein the polymeric material is at a concentration ranging from 0.0001% to about 10% w/v.

4. The cryoprotectant solution of claim 2, wherein the polymeric material is polyvinyl alcohol and wherein the polyvinyl alcohol is at a concentration ranging from 0.00001% to about 10% w/v.

5. The cryoprotectant solution of claim 4, wherein said polyvinyl alcohol is either atactic or syndiotactic.

6. The solution of claim 4, wherein the polyvinyl alcohol is about 80% hydrolyzed.

7. The cryoprotectant solution of claim 3 wherein the polymer is polyvinylpyrrolidone.

8. The cryoprotectant solution of claim 1 further comprising a component selected from the group consisting of: acetol, 3-methoxy-1,2-propanediol, sucrose, polyvinyl alcohol, polyvinyl pyrrolidone, polyethylene glycol, and dimethylfomamide.

9. The cryoprotectant solution of claim 8 wherein said polyvinyl pyrrolidone is polyvinyl pyrrolidone 5000.

10. The cryoprotectant solution of claim 8 wherein said polyethylene glycol is polyethylene glycol 1000.

11. A method of preserving a biological material comprising cells by freezing, comprising contacting the biological material with the cryoprotectant solution of claim 1, freezing the biological material in contact with the cryoprotectant solution, thawing the biological material in contact with the cryoprotectant solution, and removing the cryoprotectant solution from the thawed biological material.

12. A method of preserving biological material comprising cells by freezing point depression, comprising contacting the biological material with the cryoprotectant solution of claim 1, cooling the biological material in contact with the cryoprotectant solution to about the equilibrium freezing point of the cryoprotectant solution, storing the cooled biological material in contact with the cryoprotectant solution, warming the biological material in contact with the cryoprotectant solution sufficiently to permit removal of the cryoprotectant solution from the biological material, and removing the cryoprotectant solution.

13. A method of preserving biological material comprising cells by vitrification, comprising contacting the biological material with the cryoprotectant solution of claim 1, cooling the biological material in contact with the cryoprotectant solution to below the glass transition temperature of the cryoprotectant solution, storing the cooled biological material in contact with the cryoprotectant solution, warming the cooled biological material in contact with the cryoprotectant solution sufficiently to permit removal of the cryoprotectant solution, and removing the cryoprotectant solution from the biological material.

14. The method of claim 13, further comprising including an antifreeze protein at a concentration of about 2% w/v to 0.0001% w/v in the cryoprotectant solution.

15. The method of claim 14, further comprising including an activator for said antifreeze protein, selected from the group consisting of: gelatin, succinate, citrate, glycerol, and antibodies to the antifreeze protein.

* * * * *